United States Patent
Noda et al.

(10) Patent No.: US 11,299,742 B2
(45) Date of Patent: *Apr. 12, 2022

(54) PLANT HAVING BLUE FLOWER COLOR AND BREEDING METHOD THEREFOR

(71) Applicant: SUNTORY HOLDINGS LIMITED, Osaka (JP)

(72) Inventors: Naonobu Noda, Tsukuba (JP); Masayoshi Nakayama, Tsukuba (JP); Mitsuru Douzono, Tsukuba (JP); Satoshi Hongo, Tsukuba (JP); Ryutaro Aida, Tsukuba (JP); Yukihisa Katsumoto, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 464 days.

This patent is subject to a terminal disclaimer.

(21) Appl. No.: 16/088,943

(22) PCT Filed: Mar. 13, 2017

(86) PCT No.: PCT/JP2017/010036
§ 371 (c)(1),
(2) Date: Sep. 27, 2018

(87) PCT Pub. No.: WO2017/169699
PCT Pub. Date: Oct. 5, 2017

(65) Prior Publication Data
US 2020/0325486 A1 Oct. 15, 2020

(30) Foreign Application Priority Data
Mar. 31, 2016 (JP) .............................. JP2016-072865

(51) Int. Cl.
*C12N 15/82* (2006.01)
*A01H 6/30* (2018.01)
*A01H 6/14* (2018.01)
*A01H 6/74* (2018.01)
*A01H 5/02* (2018.01)

(52) U.S. Cl.
CPC ............. *C12N 15/825* (2013.01); *A01H 5/02* (2013.01); *A01H 6/1424* (2018.05); *A01H 6/305* (2018.05); *A01H 6/749* (2018.05)

(58) Field of Classification Search
CPC .................................................. C12N 15/825
See application file for complete search history.

(56) References Cited

U.S. PATENT DOCUMENTS

| | | | |
|---|---|---|---|
| 6,596,927 B1 | 7/2003 | Mizutani et al. | |
| 7,105,719 B1 | 9/2006 | Ashikari et al. | |
| 10,870,861 B2 * | 12/2020 | Noda | C07K 14/415 |
| 2009/0288225 A1 | 11/2009 | Noda et al. | |
| 2010/0287667 A1 | 11/2010 | Tanaka et al. | |
| 2010/0287668 A1 | 11/2010 | Tanaka et al. | |
| 2011/0055963 A1 | 3/2011 | Tanaka et al. | |
| 2011/0219476 A1 | 9/2011 | Ono et al. | |
| 2012/0096589 A1 | 4/2012 | Noda et al. | |
| 2012/0135469 A1 | 5/2012 | Ozeki et al. | |
| 2014/0033369 A1 | 1/2014 | Tanaka et al. | |
| 2015/0074855 A1 * | 3/2015 | Tanaka | C12N 9/0073 800/282 |
| 2017/0058269 A1 | 3/2017 | Tanaka et al. | |
| 2019/0032066 A1 | 1/2019 | Noda et al. | |

FOREIGN PATENT DOCUMENTS

| | | | |
|---|---|---|---|
| JP | 2005-095005 A | 4/2005 | |
| JP | 2005095005 A * | 4/2005 | |
| WO | WO-94/003606 A1 | 2/1994 | |
| WO | WO-96/025500 A1 | 8/1996 | |
| WO | WO-2000/044907 A1 | 8/2000 | |
| WO | WO-2002/086110 A | 10/2002 | |
| WO | WO-2006/046780 A1 | 5/2006 | |
| WO | WO-2006/105598 A1 | 10/2006 | |
| WO | WO-2007/046148 A1 | 4/2007 | |
| WO | WO-2008/156211 A1 | 12/2008 | |
| WO | WO-2008/156214 A1 | 12/2008 | |
| WO | WO-2010/026666 A1 | 3/2010 | |
| WO | WO-2010/069004 A1 | 6/2010 | |
| WO | WO-2010/122849 A1 | 10/2010 | |
| WO | WO-2011/016260 A1 | 2/2011 | |
| WO | WO-2012/096307 A1 | 7/2012 | |
| WO | WO-2012096307 A1 * | 7/2012 | ............. C07H 17/07 |
| WO | WO-2013/157502 A1 | 10/2013 | |

(Continued)

OTHER PUBLICATIONS

Tanaka, Yoshikazu. "Flower colour and cytochromes P450." Phytochemistry Reviews 5.2-3 (2006): 283-291. (Year: 2006).*

Tanaka, Yoshikazu, Filippa Brugliera, and Steve Chandler. "Recent progress of flower colour modification by biotechnology." International journal of molecular sciences 10.12 (2009): 5350-5369. (Year: 2009).*

Tanaka, Yoshikazu, et al. "Flower color modification by engineering of the flavonoid biosynthetic pathway: practical perspectives." Bioscience, biotechnology, and biochemistry (2010): 1007282070-1007282070. (Year: 2010).*

Brugliera, Filippa, et al. "Violet/blue chrysanthemums—metabolic engineering of the anthocyanin biosynthetic pathway results in novel petal colors." Plant and Cell Physiology 54.10 (2013): 1696-1710. (Year: 2013).*

(Continued)

*Primary Examiner* — David H Kruse
(74) *Attorney, Agent, or Firm* — Faegre Drinker Biddle & Reath LLP

(57) ABSTRACT

The purpose of the present invention is to provide a breeding method for a plant having a blue flower color with a simpler blue color development controlling technique, without requiring complex mechanisms for blue color development that have been previously presented and techniques reproducing such mechanisms. Delphinidin-based anthocyanins, in which the both 3' and 5'-positions of the anthocyanin B-ring have been glycosylated, and flavone glycosides or flavonol glycosides as copigment are made to coexist in the cells of flower organ such as petals.

24 Claims, 8 Drawing Sheets

(56) References Cited

FOREIGN PATENT DOCUMENTS

| | | |
|---|---|---|
| WO | WO-2015/167016 A1 | 11/2015 |
| WO | WO-2017/002945 A1 | 1/2017 |

OTHER PUBLICATIONS

Sasaki, Nobuhiro, and Toru Nakayama. "Achievements and perspectives in biochemistry concerning anthocyanin modification for blue flower coloration." Plant and Cell Physiology 56.1 (2015): 28-40. (Year: 2015).*

Iwashina, Tsukasa. "Contribution to flower colors of flavonoids including anthocyanins: a review." Natural product communications 10.3 (2015): 1934578X1501000335. (Year: 2015).*

Yoshiaki Kanno et al., "Chomame Yurai Anthocyanin 3',5'-O-Glucosyl-ki Ten'l Koso Idenshi o Donyu shita Keishitsu Tenakn Lobelia no Kaiseki", Dai 24 kai Japanese Society for Plant Cell and Molecular Biology Tsukuba Taikai Symposium Koen Yoshishu, 2006, p. 40, #1Aa-10.

Yoshida et al., "Blue flower color development by anthocyanins: from chemical structure to cell physiology," Natural Product Reports, vol. 26, No. 7, pp. 884-915, 2009.

Sasaki et al., "Achievements and Perspectives in Biochemistry Concerning Anthocyanin Modification for Blue Flower Coloration," Plant and Cell Physiology, vol. 56, No. 1, pp. 28-40, 2015.

Brazier-Hicks et al., "The C-Glycosylation of Flavonoids in Cereals*," The Journal of Biological Chemistry, vol. 284, No. 27, pp. 17926-17934, 2009.

Negishi et al., "Tonoplast-and Plasma Membrane-Localized Aquaporin-Family Transporters in Blue Hydrangea Sepals of Aluminum Hyperaccumulating Plant," PLOS One, vol. 7, Issue 8, pp. e43189-e43189, 2012.

Negishi et al., "Plasma membrane-localized Al-transporter from blue, hydrangea sepals is a member of the anion permease family," Genes to Cells, vol. 18, pp. 341-352, 2013.

Hirotani et al., "Cloning and expression of UDP-glucose: flavonoid 7-O-glucosyltransferase from hairy root cultures of *Scutellaria baicalensis*," Planta, vol. 210, pp. 1006-1013, 2000.

Kim et al., "Characterization of Flavonoid 7-O-Glucosyltransferase from *Arabidopsis thaliana*," Bioscience, Biotechnology, and Biochemistry, vol. 70, No. 6, pp. 1471-1477, 2006.

Saito et al., "A cyanidin glycoside giving scarlet coloration in plants of the Bromeliaceae," Phytochemistry 22:1735-1740, 1983.

Andersen et al., "The Anthocyanins," in *Flavonoids, Chemistry, Biochemistry and Applications*, Edited by Andersen, O.M. & Markham, K.R., Taylor & Francis, 2006, pp. 471-537.

Shimizu-Yumoto et al., "Slantingly cross loading sample system enables simultaneous performance of separation and mixture to detect molecular interactions on thin-layer chromatography," J. Chromatogr. A, 1245:183-189, 2012.

Saito et al., "Covalent anthocyanin-flavonol complexes from the violet-blue flowers of *Allium* 'Blue Perfume'," Phytochemistry 80:99-108, 2012.

Falginella et al., 2010, Expansion and subfunctionalisation of flavonoid 3',5'-hydroxylases in the grapevine lineage, BMC Genomics 11:562, 1-18.

Naonobu Noda et al., "Genetic Engineering of Novel Bluer-Colored Chrysanthemums Produced by Accumulation of Delphinidin-Based Anthocyanins," Plant Cell Physiology, 2013, pp. 1684-1695, vol. 54, No. 10.

Kogawa, K., et al., "Purification and characterization of UDP-glucose: anthocyanin 3',5'-O-glucosyltransferase from *Clitoria tematea*," Planta, 2007, 226:1501-1509.

Keskin et al., 2004, Protein Science 13: 1043-1055.

Thornton et al., 2000, Nature Structural Biology, structural genomic supplement, Nov. 2000: 991-994.

Guo et al., 2004, Proceedings of the National Academy of Sciences USA 101: 9205-9210.

Tanaka et al., 2009, Recent Progress of Flower Colour Modification by Biotechnology, Int. J. Mol. Sci. 10: 5350-5369.

Fukuchi-Mizutani et al., 2003, Plant Physiology 132: 1652-1663.

International Search Report dated Sep. 27, 2016 for PCT/JP2016/069536.

Noda N. et al., "Generation of blue chrysanthemums by anthocyanin B-ring hydroxylation and glycosylation and its coloration mechanism," Sci. Adv. 3:e1602785 (2017).

\* cited by examiner

PLANT HAVING BLUE FLOWER COLOR AND BREEDING METHOD THEREFOR

CROSS REFERENCE TO RELATED APPLICATIONS

This application is the National Stage of International Application No. PCT/JP2017/010036 filed Mar. 13, 2017 and claims benefit of Japanese Application No. 2016-072865 filed on Mar. 31, 2016.

FIELD

The present invention relates to a method of creating plants with blue flower color, comprising making deiphinidin-based anthocyanins having glycosyl groups at both the 3'- and 5'-positions of the anthocyanin B-ring coexist with copigments (flavone glycoside or flavonol glycoside) in plant cells, and to plants with blue flower color, in which deiphinidin-based anthocyanins having glycosyl groups at both the 3'- and 5'-positions of the anthocyanin B-ring and copigments (flavone glycoside or flavonol glycoside) coexist in the cells, or its inbred or outbred progeny, or their propagules, partial plant bodies (especially cut flowers) or processed forms thereof (especially processed cut flowers), tissue or cells.

BACKGROUND

*Chrysanthemum*, rose, carnation and lily are industrially important ornamental plants worldwide. Among such major ornamental plants, however, none of the hybridizable related species have wild species with blue flower color, which has made it difficult to create varieties with blue flower color by conventional cross-breeding and mutation breeding. In this regard, the present inventors have recently succeeded in creating "blue *chrysanthemum*" (PTL 2) having flower colors that are true blue colors, such as Violet-Blue95, Violet-Blue97 and Blue100, based on the Royal Horticultural Society Colour Chart (RHSCC), by a method of gene transfer of *Campanula* F3'5'H and *Clitoria* A3'5'GT, which are bluer flower colors than transfer of *Campanula* F3'5'H alone (PTL 1). For other major ornamental plants such as rose, lily, carnation, dahlia and *Phalaenopsis aphrodite*, however, no varieties have yet been created with the same degree of blue as "blue chrysanthemum", and methods are being sought for creation of their blue flowers.

Genes introduced during flower color modification by gene recombination with the aim of conversion to blue flower color, have been selected based on knowledge of the mechanism of blue color development in blue flowers of nature. Since the anthocyanins that accumulate in most blue flowers have delphinidin-based aglycones, the flavonoid 3',5'-hydroxylase gene responsible for its biosynthesis is introduced for modification of the flower color, in order to create blue flowers (PTL 3). On the other hand, flowers exhibiting pink, reddish purple, purple and violet colors, though with delphinidin-based anthocyanins, are abundant in wild species. It has been reported that the mechanism of blue color development in flowers also requires intramolecular association (intramolecular copigmentation) with aromatic acyl groups of anthocyanin, intermolecular association (intermolecular copigmentation) with flavonoids, acylquinates or other compounds, interaction with metal ion, metal complex formation and increase in vacuolar pH, in addition to production of delphinidin-based anthocyanins (NPL 1).

When polyacylated delphinidin-based anthocyanins modified with two or more aromatic acyl groups and glycosyl groups accumulate in petals, blue color is exhibited by intramolecular association. Related enzyme genes such as the glucosyltransferase gene and aromatic acyltransferase gene have been reported from Gentian (PTLs 4 and 5), Delphinium (PTL 6, NPL 2) and *Clitoria* (PTLs 2 and 7), which exhibit blue flower colors by this mechanism. For intermolecular association (copigmentation), enzyme genes involved in C-glycosylflavone biosynthesis (NPL 3) and genes that allow flavone synthesis in rose (PTL 8) have been reported as effective copigments for blue color development when coexist with anthocyanins. For metal ion interaction, involvement of iron ions in tulip and aluminum ions in hydrangea have been reported, while a gene that transports metal ions into anthocyanin-accumulating vacuoles has also been reported (NPL 4). For metal complex formation, flavonoid 7-glycosyltransferase genes from skullcap (*Scutellaria baicalensis*) and *Arabidopsis thaliana* (NPL 5) and a 4',7-glycosyltransferase genes from *Nemophila* (PTL 9) have been reported for regulation of the glycosylation pattern of flavones, thought to be necessary for formation of metal complexes. There have also been reported glucosyltransferase genes that further glycosylation at the 3-glycosyl group of anthocyanin, and acyltransferase genes that transfer an acyl group of an organic acid to the glycosyl group of anthocyanin, as genes that participate in intramolecular association, intermolecular association or metal complex formation. The promoters and terminators that are effective for expressing transgenes in the petals of major ornamental plants are being elucidated. Thus, it is thought to be theoretically possible to transfer genes involved in mechanisms of blue color development, and to function them in ornamental plants.

Although ornamental plants having blue flower colors have been created by genetic engineering methods and such carnations and roses are commercially available, their flower colors are purple (RHSCC color hue group: Purple) or violet (Purple-Violet, Violet), whereas blue ornamental plants having Violet-Blue or Blue flower colors have not been created, other than "blue chrysanthemum" (PTL 2). Attempts have therefore been made to isolate the related genes and transfer them in combinations in order to organize the various mechanisms of blue color development (NPL 1) in ornamental plants such as carnation, lily or rose, but these attempts have not yet led to creation of blue flowers. This is because the structures of polyacylated anthocyanins and metal complexes that are responsible for most blue flower color development are complex, and numerous exogenous genes are necessary for their synthesis. There are limited cases where a series of genes responsible for blue color development have been isolated from blue flowers in nature. The only completely obtained gene set known to be necessary for gene introduction for blue color development is the polyacylated anthocyanin biosynthesis genes of Gentian. Even if all of the genes necessary for blue color development are completely obtained, it is still difficult to create blue flowers, because of the complexity of the introduction and regulation of numerous exogenous genes.

CITATION LIST

Patent Literature

[PTL 1] International Patent Publication No. WO2010/122849
[PTL 2] International Patent Publication No. WO2017/002945
[PTL 3] International Patent Publication No. WO2010/069004
[PTL 4] International Patent Publication No. WO1996/025500
[PTL 5] International Patent Publication No. WO2006/046780
[PTL 6] International Patent Publication No. WO2011/016260
[PTL 7] International Patent Publication No. WO2007/046148
[PTL 8] International Patent Publication No. WO2008/156211
[PTL 9] International Patent Publication No. WO2012/096307
[PTL 10] International Patent Publication No. WO2002/086110
[PTL 11] International Patent Publication No. WO2000/044907
[PTL 12] International Patent Publication No. WO1994/003606
[PTL 13] International Patent Publication No. WO2013/157502
[PTL 14] International Patent Publication No. WO2006/105598

Non Patent Literature

[NPL 1] Nat. Prod. Rep. (2009)26:884
[NPL 2] Plant Cell Physiol. (2015) 56:28
[NPL 3] J Biol. Chem. (2009) 284:17926
[NPL 4] Plos one (2012)7:e43189, Genes to Cells (2013) 18:341
[NPL 5] Planta (2000) 210:1006, Biosci. Biotechnol. Biochem. (2006) 70:1471
[NPL 6] Saito et al., (1983) A cyanidin glycoside giving scarlet coloration in plants of the Bromeliaceae., Phytochemistry 22:1735-1740
[NPL 7] Andersen et al., The anthocyanins, in Flavonoids, Chemistry, biochemistry and applications, Edited by Andersen, O. M. & Markham, K. R., Taylor & Francis, pp. 472-537 (2006)
[NPL 8] Shimizu-Yumoto et al., (2012) Slantingly cross loading sample system enables simultaneous performance of separation and mixture to detect molecular interactions on thin-layer chromatography. J. Chromatogr. A, 1245: 183-189

SUMMARY

Technical Problem

It is an object of the invention to provide a method of creating a plant having a blue flower color (RHS Colour Chart, 5th Edition: Violet-Blue group/Blue group and/or hue angle: 230° to 290°), based on a technique for regulating blue color development that is completely different from the theory and technique of the prior art.

Solution to Problem

As a result of much diligent research and experimentation with the aim of achieving the object stated above, the present inventors have obtained the surprising knowledge that a plant with blue flower color can be created by making a delphinidin-based anthocyanins having glycosyl groups at both the 3'- and 5'-positions of the anthocyanin B-ring coexist with copigments (flavone glycoside or flavonol glycoside) in plant cells, without modification with an aromatic organic acid, and the invention has been completed based on this knowledge.

Specifically, the present invention provides the following.

[1] A method of creating a plant with a blue flower color, comprising making delphinidin-based anthocyanins having glycosyl groups at both 3'- and 5'-positions of the anthocyanin B-ring coexist with copigments (flavone glycoside or flavonol glycoside) in plant cells.

[2] The method according to [1], wherein the flavone glycoside is selected from the group consisting of luteolin glycoside, tricetin glycoside, apigenin glycoside, acacetin glycoside, and their combinations.

[3] The method according to [2], wherein the luteolin glycoside is luteolin 7-malonyl glucoside, luteolin 7-glucoside, luteolin 7,3'-diglucoside, luteolin 8-C-glucoside or luteolin 6-C-glucoside, or a derivative thereof.

[4] The method according to [2], wherein the tricetin glycoside is tricetin 7-malonyl glucoside or a derivative thereof.

[5] The method according to [2], wherein the apigenin glycoside is apigenin 7-glucoside, apigenin 7-rutinoside, apigenin 8-C-glucoside or apigenin 6-C-glucoside, or a derivative thereof.

[6] The method according to [2], wherein the acacetin glycoside is acacetin 7-rutinoside or a derivative thereof.

[7] The method according to [1], wherein the flavonol glycoside is selected from the group consisting of kaempferol glycoside, quercetin glycoside, and their combinations.

[8] The method according to [7], wherein the kaempferol glycoside is kaempferol 3-glucoside or a derivative thereof.

[9] The method according to [7], wherein the quercetin glycoside is quercetin 3-glucoside, quercetin 3-(6"-malonyl) glucoside or quercetin 3-rutinoside, or a derivative thereof.

[10] The method according to any one of [1] to [9], wherein the delphinidin-based anthocyanins having glycosyl groups at both the 3'- and 5'-positions of the anthocyanin B-ring are selected from the group consisting of delphinidin 3-(6"-malonyl)glucoside-3',5'-diglucoside (ternatin C5), delphinidin 3,3',5'-triglucoside (preternatin C5), and their combinations.

[11] The method according to any one of [1] to [10], wherein the delphinidin-based anthocyanins having glycosyl groups at both the 3'- and 5'-positions of the anthocyanin B-ring and the flavone glycoside coexist in a quantity ratio of 1:1 to 1:10.

[12] The method according to any one of [1] to [11], wherein the intravacuolar pH of the plant is 5.2 to 6.4.

[13] The method according to any one of [1] to [12], wherein the plant is rose, lily, carnation, dahlia, *Phalaenopsis aphrodite* or chrysanthemum.

[14] A plant with a blue flower color wherein a delphinidin-based anthocyanins having glycosyl groups at both the 3'- and 5'-positions of the anthocyanin B-ring coexists with a copigment (flavone glycoside or flavonol glycoside) in the plant cells, or its inbred or outbred progeny.

[15] The plant according to [14], or its inbred or outbred progeny, wherein the flavone glycoside is selected from the group consisting of luteolin glycoside, tricetin glycoside, apigenin glycoside, acacetin glycoside, and their combinations.

[16] The plant according to [15], or its inbred or outbred progeny, wherein the luteolin glycoside is luteolin 7-malonyl glucoside, luteolin 7-glucoside, luteolin 7,3'-diglucoside, luteolin 8-C-glucoside or luteolin 6-C-glucoside, or a derivative thereof.

[17] The plant according to [15], or its inbred or outbred progeny, wherein the tricetin glycoside is tricetin 7-malonyl glucoside or a derivative thereof.

[18] The plant according to [15], or its inbred or outbred progeny, wherein the apigenin glycoside is apigenin 7-glucoside, apigenin 7-rutinoside, apigenin 8-C-glucoside or apigenin 6-C-glucoside, or a derivative thereof.

[19] The plant according to [15], or its inbred or outbred progeny, wherein the acacetin glycoside is acacetin 7-rutinoside or a derivative thereof.

[20] The plant according to [14], or its inbred or outbred progeny, wherein the flavonol glycoside is selected from the group consisting of kaempferol glycoside, quercetin glycoside, and their combinations.

[21] The plant according to [20], or its inbred or outbred progeny, wherein the kaempferol glycoside is kaempferol 3-glucoside or a derivative thereof.

[22] The plant according to [20], or its inbred or outbred progeny, wherein the quercetin glycoside is quercetin 3-glucoside, quercetin 3-(6"-malonyl) glucoside or quercetin 3-rutinoside, or a derivative thereof.

[23] The plant according to any one of [14] to [22], or its inbred or outbred progeny, wherein the delphinidin-based anthocyanins having glycosyl groups at both the 3'- and 5'-positions of the anthocyanin B-ring are selected from the group consisting of delphinidin 3-(6"-malonyl)glucoside-3',5'-diglucoside (ternatin C5), delphinidin 3,3',5'-triglucoside (preternatin C5), and their combinations.

[24] The plant according to any one of [14] to [23], or its inbred or outbred progeny, wherein the delphinidin-based anthocyanins having glycosyl groups at both the 3'- and 5'-positions of the anthocyanin B-ring and the flavone glycoside or flavonol glycoside coexist in a quantity ratio of 1:1 to 1:10.

[25] The plant according to any one of [14] to [24], or its inbred or outbred progeny, wherein the intravacuolar pH of the plant is 5.2 to 6.4.

[26] The plant according to any one of [14] to [25], or its inbred or outbred progeny, wherein the plant is rose, lily, carnation, dahlia, Phalaenopsis aphrodite or chrysanthemum.

[27] Propagules, partial plant bodies, tissue or cells of a plant according to any one of [14] to [26], or its inbred or outbred progeny.

[28] Cut flowers of a plant according to any one of [14] to [27], or its inbred or outbred progeny, or a processed form created from the cut flowers.

Advantageous Effects of Invention

According to the invention it is possible to create varieties having blue flower colors (RHS Colour Chart 5th Edition: Violet-Blue group/Blue group and/or hue angle: 230° to 290°), not only in chrysanthemum but also in other major ornamental plants such as rose, lily, carnation, dahlia and Phalaenopsis aphrodite, which has not been possible in the prior art. In particular, it is possible to create a "blue flower" by the simple method of glycosylating only both 3'- and 5'-positions of the anthocyanin B-ring in a flower containing a flavone glycoside or flavonol glycoside as suitable copigments.

BRIEF DESCRIPTION OF DRAWINGS

FIG. 2a shows the results (under a fluorescent lamp) of developing blue chrysanthemum petal extract by cross-TLC. FIG. 2b shows the results (under UV light (365 nm)) of developing blue chrysanthemum petal extract by cross-TLC. The A bands include the B-ring glycosylated anthocyanins (ternatin C5 and preternatin C5). The blue-colored portions in the A bands are indicated by gray arrows. The C1 bands exhibiting yellow fluorescence under UV light cross in the portions of the gray arrows. The bands C2 (broken lines) that are dark under UV light cross in the purple-colored portions, even in the A bands. C1 and C2 include copigment substances that convert A to blue and violet, respectively. FIGS. 2a and 2d show the identified structures of C1 and C2. The arrows indicate HMBC.

Figure 1:
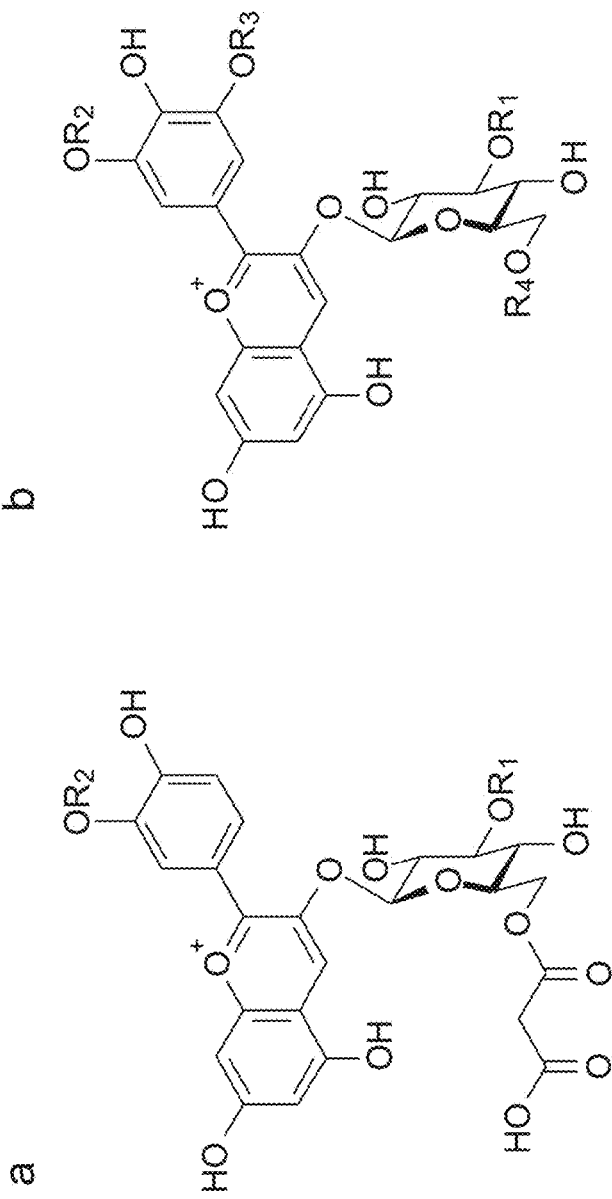
FIG. 1 shows anthocyanins: a) cyanidin-based anthocyanins (A1 to A4) and b) delphinidin-based anthocyanins (A5 to A10) that are present in petals of host chrysanthemum and gene recombinant chrysanthemum with blue flower color.

The present invention relates to a method of creating a plant with a blue flower color, comprising making delphinidin-based anthocyanins having glycosyl groups at both the 3'- and 5'-positions of the anthocyanin B-ring coexist with copigments (flavone glycoside or flavonol glycoside) in plant cells.

Anthocyanins are a group of pigments that are widely distributed in higher plants, and they are known to exhibit red, purple and blue flower colors. They are classified into 3 types, pelargonidin, cyanidin and delphinidin, based on the number of hydroxyl groups on the B-ring of the anthocyanidin, as the aglycone form. The chromophoric group is the aglycone portion, pelargonidin exhibiting orange red color, cyanidin exhibiting red color and delphinidin exhibiting purplish red color. Anthocyanins having glycosyl groups at both the 3'-position or 5'-position of the B-ring, as the major pigment of blue chrysanthemum petals, are known to have the absorption maximum wavelength in the absorption spectrum under acidic conditions shifted toward the short wavelength end, compared to non-glycosylated anthocyanins (NPL 6), and it has been reported that accumulation of B-ring glycosylated anthocyanins in petals produces a red colored flower (NPL 7).

The present inventors have found that blue chrysanthemum, created by expressing both the *Campanula* F3'S'H gene and the *Clitoria* A3'S'GT gene in chrysanthemum petals (PTL 2), includes delphinidin 3-(6"-malonyl)glucoside-3',5'-diglucoside (ternatin C5, TC5) as the major pigment, while also including as trace pigments, delphinidin 3,3',5'-triglucoside (preternatin C5, pTC5) which are demalonylated forms of ternatin C5, delphinidin 3-(3",6"-dimalonyl)glucoside-3',5'-diglucoside, delphinidin 3-(6"-malonyl)glucoside-3'-glucoside (Dp3MG3'G) and cyanidin 3-(6"-malonyl)glucoside-3'-glucoside (Cy3MG3'G). Ternatin C5, as the major anthocyanin of blue chrysanthemum, has a visible absorption maximum wavelength of 511 nm in HPLC analysis under acidic conditions, which is shifted to the short wavelength end with respect to the absorption maximum wavelength of 518 nm exhibited by cyanidin 3-(6"-malonyl)glucoside (Cy3MG), as the major anthocyanin of host red or pink chrysanthemums. This means that, although ternatin C5 is redder than the original cyanidin-based anthocyanin pigment, it develops blue color in chrysanthemum petals. No case has yet been reported wherein blue color is developed in flower petals by reddish anthocyanin having glucosyl group at both 3'- and 5'-hydroxyl groups of the anthocyanin B-ring, such as ternatin C5.

When anthocyanin pigments coexist with substances such as flavones, flavonols, organic acid esters and tannins, their molecular interaction often develops blueish colors. This phenomenon is known as copigmentation (copigment effect, intermolecular copigmentation, or intermolecular association), and substances producing the phenomenon are called copigments. Copigmentation includes not only a bathochromic shift that induces blue coloration, but also a hyperchromic effect or an effect of increasing color stability. The present inventors therefore surmised that in blue chrysanthemum, petal blue color development is achieved by the interaction of a delphinidin-based anthocyanins having glycosyl groups at both the 3'- and 5'-positions of the anthocyanin B-ring, such as ternatin C5, preternatin C5 or delphinidin 3-(3",6"-dimalonyl)glucoside-3',5'-diglucoside, and a plant-endogenous copigment substances.

Throughout the present specification, the "delphinidin-based anthocyanins having glycosyl groups at both the 3'- and 5'-positions of the anthocyanin B-ring" is not particularly restricted so long as it can coexist with flavone glycosides or flavonol glycosides to develop bluish color, and examples include ternatin C5 and preternatin C5. Also, delphinidin 3-(3",6"-dimalonyl)glucoside-3',5'-diglucoside, which has been found to accumulate in petals of transgenic blue chrysanthemum, is thought to exhibit blue color by coexistence with flavone glycosides or flavonol glycosides.

Flavones are organic compounds that are flavan-derived cyclic ketones, and in plants they mainly exist as glycosides. Flavone, in the strict definition, refers to 2,3-didehydroflavan-4-one, which is a compound with chemical formula $C_{15}H_{10}O_2$ and molecular weight 222.24, but in the wider sense flavones are a category of flavonoids, a flavonoid being classified as a "flavone" if it has a flavone structure as the basic backbone and also lacks the hydroxyl group at the 3-position. Throughout the present specification, "flavone glycoside" refers to the wider definition of flavone, i.e. a glycoside of a derivative belonging to the flavones. Flavone glycosides include, but are not limited to, luteolin glycoside, tricetin glycoside, apigenin glycoside and acacetin glycoside. Luteolin glycoside, tricetin glycoside, apigenin glycoside and acacetin glycoside also include glycosides of derivatives of luteolin, tricetin, apigenin and acacetin. Examples of luteolin glycosides include luteolin 7-(6"-malonyl)glucoside (Lt7MG), luteolin 7-glucoside (cynaroside), (cynaroside), luteolin 7,3'-diglucoside, luteolin 8-C-glucoside (orientin), luteolin 6-C-glucoside (isoorientin) or their derivatives, compounds of tricetin glycosides include tricetin 7-(6"-malonyl)glucoside (Tr7MG) or its derivatives, examples of apigenin glycosides include apigenin 7-glucoside (cosmosiin), apigenin 7-rutinoside (isorhoifolin), apigenin 8-C-glucoside (vitexin), apigenin 6-C-glucoside (isovitexin) or their derivatives, and compounds of acacetin glycosides include acacetin 7-rutinoside (linarin) or its derivatives.

Flavonols are a category of flavonoids having the 3-hydroxyflavone (3-hydroxy-2-phenylchromen-4-one) backbone. In plants they exist mainly as glycosides. Throughout the present specification, "flavonol glycoside" means a glycoside of a derivative belonging to flavonols. Flavonol glycosides include, but are not limited to, kaempferol glycoside, quercetin glycoside and myricetin glycoside. Kaempferol glycoside, quercetin glycoside and myricetin glycoside also include glycosides of derivatives of kaempferol, quercetin and myricetin. Examples of kaempferol glycosides include kaempferol 3-glucoside, kaempferol 3-rutinoside, and their derivatives, and examples of quercetin glycosides include quercetin 3-glucoside, quercetin 3-(6"-malonyl) glucoside, quercetin 3-rutinoside, and their derivatives.

Flavones are synthesized in the petals of numerous plants including chrysanthemum, carnation and gerbera, and accumulate as glycosides, but in some plants such as rose, lily or lisianthus (*Eustoma*), flavones are not detected in the petals and only accumulate in trace amounts. The flavone synthase gene can be used to synthesize and accumulate flavone aglycones and the glycosides in the petals of such plants. For example, genes coding for an oxoglutaric acid-dependent dioxygenase, flavone synthase I (FNSI) (PTL 10) and genes encoding for an NADPH-dependent cytochrome P450, flavone synthase II (FNSII) (PTL 11) have been cloned from various plant species. Thus, genetic transformation of these genes allows synthesis of flavone glycoside and their accumulation in petals, even in plants where flavone glycosides are not detected in the petals, such as rose (PTL 8). Flavonols are also synthesized in the petals of numerous plants including rose, lily and lisianthus (*Eustoma*), accumulating as glycosides, but in some plants such as chrysanthemum, carnation and gerbera, flavonols are not detected in the petals and only accumulate in trace amounts. The flavonol synthase (FLS) gene can be used to synthesize and accumulate flavonol glycosides in the petals of such plants. The genes encoding for flavonol synthase, an oxoglutaric acid-dependent dioxygenase have been cloned from various plant species (PTL 12). Thus, genetic transformation of these genes allows synthesis and accumulation of flavonol glycosides in petals, even in plants where flavonol glycosides are not detected in the petals, such as chrysanthemum. There are no particular restrictions on plants that may be used for the invention, and examples include rose, lily, carnation, dahlia, *Phalaenopsis aphrodite* and chrysanthemum, but a variety of different plants may be used, such as lisianthus, cyclamen, statice, cymbidium, gerbera, dendrobium, tulip, pelargonium, petunia and cattleya, for which methods of genetic transformation have been reported.

In flavone accumulating plants, the coexistence of 3',5'-diglycosylated delphinidin-based anthocyanins and flavone glycosides can be achieved in the cells by the only additional glycosylation at the 3'- and 5'-positions of anthocyanin B-ring. The 3',5'-O-glycosylation of the anthocyanin B-ring can be achieved by introducing the *Clitoria*-derived anthocyanin 3',5'-O-glucosyl transferase (CtA3'5'GT) gene into the plant (PTL 2). The other gene encoding anthocyanin 3',5'-O-glucosyltransferase can also be cloned from plants containing 3',5'-O-glycosylated anthocyanins. The *Campanula*-derived flavonoid 3',5'-hydroxylase gene (CamF3'5'H) (PTL 13) may be also coexpressed with CtA3'5'GT gene (PTL 2).

In order to transfer exogenous genes into plant and express the transgene in a constitutive or tissue-specific manner, any method publicly known to those skilled in the art under current technical standards, such as the *Agrobacterium*-mediated transformation binary vector method, electroporation, polyethylene glycol (PEG) method or particle bombardment may be used.

The delphinidin-based anthocyanins having glycosyl groups at the 3'- and 5'-positions of the anthocyanin B-ring and flavone glycosides will typically be coexisting in a quantity ratio of 1:1 to 1:10, preferably 1:5 to 1:10 and optimally about 1:10, to allow development of blue color.

Coloration through intermolecular copigmentation of anthocyanins and copigments is governed by pH. The pH in the organelles such as vacuoles where the pigments accumulate can be measured directly by insertion of electrodes. The approximate pH value can also be measured by measuring the pH of juice squeezed from the petal tissues. If the pH of the vacuole in which the anthocyanins and the copigments coexist is not suitable for blue color development, it can be optimized by introducing and function the exogenous gene for the regulation of pH. The vacuolar acidification is controlled by the function of vacuolar proton pumps such as vacuolar-type HtATPases (V-ATPase) and vacuolar-type Htpyrophosphatases (V-PPase) present in the vacuole membranes. Therefore, the vacuolar pH can be regulated by promoting or inhibiting the functions of these proteins (PTL 14). Also, in morning glory wherein the pH increases from 6.6 to 7.7 at the time of flowering, causing the flower color to change from purple to blue, a gene coding for the sodium ion-hydrogen ion antiporter (NHX), which increases the pH by discharging proton ions during transport of potassium ions into the vacuoles, has been reported (NPL 1), and this allows regulation of the intravacuolar pH to facilitate production of blue color. The intravacuolar pH that exhibits blue color is typically about 5.2 to 6.4, preferably about 5.4 to 6.2 and optimally about 5.6 to 6.0, but there is no limitation to this range so long as blue color is exhibited.

The present invention further relates to cut flowers of a plant with a blue flower color obtained by the method described above or its inbred or outbred progeny, or a processed form created from the cut flowers (especially processed cut flowers). The processed cut flowers referred to here include pressed flowers formed using cut flowers, or preserved flowers, dry flowers or resin sealed products, with no limitation to these.

EXAMPLES

Example 1: Identification of Delphinidin Glycosides with Glucoses Bonded to the 3'- and 5'-Hydroxyl Groups of the B-Ring, Accumulated in Blue Chrysanthemum Petals The major anthocyanins of "Taihei" transformants exhibiting blue color, obtained by transformation using *Agrobacterium* in which binary vector pB423 coexpressing *Campanula*-derived F3'5'H (CamF3'5'H; PTL 13; GenBank accession number: FW570877) and CtA3'5'GT coding for *Clitoria*-derived anthocyanin 3',5'-O-glucosyltransferase (PTL 2; GenBank accession number: AB115560) had been introduced, were analyzed by LC-MS. The flower color of the chrysanthemum ligulate petals used was measured using the Royal Horticultural Society Colour Chart (RHSCC), 5th Edition, with comparison under a fluorescent light, and they were found to have blue flower color corresponding to Violet-Blue 97 or Blue 100. The L* value (lightness), a* value (redness/greeness) and b* value (yellowness/blueness) according to the CIEL*a*b* color system were measured using a CD100 colorimeter (Yokogawa Test & Measurement Corp.), the average value of at least 3 measurements was calculated, and the hue angle was calculated based on the obtained value, indicating a blue color hue angle value of 230-290°. LC-MS analysis was performed using an ACQUITY UPLC BEH C18 column (1.7 μm, 2.1 i.d.×100 mm, Waters), fractionation was carried out with an ACQUITY UPLC at 35° C., and detection was performed with an ACQUITY UPLC photodiode array (PDA) detector and an ACQITY tandem quadrupole mass spectrometer (TQD) (Waters). A 1% aqueous formic acid solution (solvent A) and 1% formic acid-containing acetonitrile (solvent B) were used as the UPLC mobile phases. The flow rate of the mobile phase was 0.1 ml/min, and 0 to 5% B (0-5 min), 5% to 35% B (5-20 min), 35% B (20-25 min) gradient elution was performed. PDA detection was performed at 200 to 800 nm, and chromatogram for flavonoid and acylquinic acid was obtained at 360 nm while chromatogram for anthocyanin was obtained at 530 nm. The mass spectrometer analysis conditions were as follows: ESI positive ion mode, capillary voltage=3.5 kV; cone voltage=45 V; source temperature=150° C.; desolvation temperature=350° C.; desolvation gas flow rate=500 L/h; cone gas flow rate=50 L/h; collision energy=6 V, 20 V; measuring mass range=180-1080 m/z. As the result of analysis of the chromatogram with a detection wavelength of 530 nm, the major anthocyanin pigments were A7 and A8. Also, eight anthocyanin components including A3 (A1-6, A9-10, FIG. 1) were detected as minor pigments.

As the result of LC-MS/MS analysis of A8, m/z=875[M]$^+$ was obtained as the precursor ion, and m/z=713 (-glucose), 627 (-glucose-malonyl), 465 (−2×Glc-malonyl) and 303 (−3×Glc-malonyl; delphinidin) as product ions. Also, isolation and purification from the petals and measurement of the $^1$H-NMR and NOESY spectra (Table 1) and the high-resolution ESI-TOF-MS spectrum (Table 2), allowed identification as ternatin C5 (delphinidin 3-(6"-maonyl)glucoside-3',5'-diglucoside) (FIG. 1). As a result of LC-MS/MS analysis of A7, m/z=789[M]$^+$ was obtained as the precursor ion and 627 (-Glc), 465 (-2×glucose) and 303 (-3×glucose) as product ions, and the acid hydrolysis product of A8, and matching with the HPLC retention time and spectrum, suggested that it was preternatin C5 (delphinidin 3,3',5'-triglucoside) (FIG. 1). As a result of LC-MS analysis of A3 that was detected as a trace anthocyanin in blue flower petals, m/z=773[M]+ was obtained as the precursor ion. Isolation and purification from the petals, followed by NMR analysis ($^1$H-NMR, NOESY) and precision mass analysis identified it as cyanidin 3-(6"-maonyl)glucoside-3'-glucoside (Cy3MG3'G) (FIG. 1, Table 1, Table 2).

TABLE 1

$^1$H (600 MHz) NMR spectral data for isolated anthocyanins

| | A3 | | A8 | |
|---|---|---|---|---|
| Position | δH | J(Hz) | δH | J(Hz) |
| Aglycone | | | | |
| 1 | — | | — | |
| 2 | — | | — | |
| 3 | — | | — | |
| 4 | 8.86 | s | 9.00 | s |
| 5 | — | | — | |
| 6 | 6.70 | s | 6.68 | br s |
| 7 | — | | — | |
| 8 | 6.96 | s | 7.03 | br s |
| 9 | — | | — | |
| 10 | — | | — | |
| 1' | — | | — | |
| 2' | 8.19 | br s | 8.23 | s |
| 3' | — | | — | |
| 4' | — | | — | |
| 5' | 7.03 | d | 8.3 | — |
| 6' | 8.39 | d | 9.0 | 8.23 | s |
| 3-O-glucosyl | | | | |
| 1 | 5.24 | d | 7.2 | 5.25 | d | 7.2 |
| 2 | 3.49 | t | 8.4 | 3.56-3.63 | m |
| 3 | 3.37-3.43 | m | | 3.56-3.63 | m |
| 4 | 3.25 | t | 8.7 | 3.54 | t | 9.3 |
| 5 | 3.73 | t | 8.4 | 3.91 | m |
| 6a | 4.44 | d | 12.0 | 4.53 | br d | 11.4 |
| 6b | 4.11 | dd | 7.5, 11.7 | 4.29 | dd | 7.5, 11.7 |
| 3'-O-glucosyl and 5'-O-glucosyl | | | | |
| 1 | 4.95 | d | 7.2 | 5.08 | d | 6.0 |
| 2 | 3.37-3.43 | m | | 3.56-3.63 | m |
| 3 | 3.37-3.43 | m | | 3.56-3.63 | m | 9.3 |
| 4 | 3.25 | t | 8.7 | 3.46 | t | 9.3 |
| 5 | 3.49 | t | 8.4 | 3.72 | t | 7.8 |
| 6a | 3.81 | d | 11.4 | 3.96 | d | 12.0 |
| 6b | 3.59 | dd | 2.7, 11.4 | 3.78 | dd | 5.7, 12.3 |

A3: in DMSO-d6 + TFA
A8: in CD$_3$OD + TFA

Example 2: Relationship Between Proportions of Delphinidin Glycosides Having Glucoses Bonded to 3'- and 5'-Hydroxyl Groups of B-Ring in Petals, and Blue Color Development The flower color, anthocyanin composition and transgene expression of a transformant line obtained by genetic transformation of CamF3'5'H gene and CtA3'5'GT gene into the decorative pink cultivar "Sei Arabella" were analyzed. Flowers with cyanidin-based anthocyanin as the major anthocyanin, despite 3'-glycosylation, exhibited pink color similar to the host flower color, though with a slight violet tint. Flowers with delphinidin-based anthocyanins as the major anthocyanin exhibited purple or blue color, which were bluer than the host flower color. The blue color tone was stronger with a higher proportion of 3',5'-diglucosylated anthocyanins. A correlation was seen between the proportion of delphinidin-based anthocyanins and the CamF3'5'H expression level, and the proportion of 3'- and/or 5'-glycosylated anthocyanins and the CtA3'5'GT expression level. These results demonstrated that the 3',5'-diglucosylated delphinidin-based anthocyanins A7 and A8 are responsible for blue color development.

Example 3: Difference Between Absorption Spectra of Solution of Delphinidin Glycosides Having Glucoses Bonded to 3'- and 5'-Hydroxyl Groups of B-Ring, in Solution and in Chrysanthemum Petals The absorption spectrum of chrysanthemum ray florets was measured using a UV-2450 spectrophotometer (Shimadzu Corp.) with a mounted ISR-2200 integrating sphere accessory. The visible light range absorption maximum of the pink petals of the host cultivar "Sei Arabella" ($\lambda_{vismax}$) was 556 nm, and the $\lambda_{vismax}$ of a violet recombinant was in the longer wavelength range of 561 nm. The $\lambda_{vismax}$ of a blue recombinant was further in the long wavelength range at 573 nm, with a characteristic shoulder region near 615 nm. In HPLC measurement under acidic conditions, the $\lambda_{vismax}$ of the major pigments A1, A2 of the host with pink flower color was 518 nm, while the $\lambda_{vismax}$ of the major pigment A5 of the violet recombinant was 527 nm. The $\lambda_{vismax}$ of A8, as the major anthocyanin of the blue recombinant, was in a shorter wavelength range than A1 or A2, at 511 nm. After dissolving each of the major anthocyanins in acetate buffer at pH 5.6, which is the pH of juice squeezed from the petals, the $\lambda_{vismax}$ of A1 was 533 nm. The $\lambda_{vismax}$ of A5 was 535 nm, and a shoulder region near 570 nm was observed. The $\lambda_{vismax}$ of A8 was 561 nm, and a shoulder region near 590 nm was observed. Although A8 had a $\lambda_{vismax}$ with a shorter wave-

TABLE 2

HR-MS results for isolated anthocyanins and flavones

| Compound name | | Detection ion | M/z | Calculated value | Molecular formula |
|---|---|---|---|---|---|
| A3 | Cyanidin 3-(6"-malonyl)glucoside-3'-glucoside | [M]+ | 697.1605 | 697.1616037 | $C_{30}H_{33}O_{19}$ |
| | | [M − H + Na]+ | 719.1781 | 719.1435487 | $C_{30}H_{32}O_{19}Na$ |
| A8 | Delphinidin 3-(6"-malonyl)glucoside-3',5'-diglucoside (ternatin C5) | [M]+ | 875.2628 | 875.2093417 | $C_{36}H_{43}O_{25}$ |
| | | [M − H + Na]+ | 897.1888 | 897.1912867 | $C_{36}H_{42}O_{25}Na$ |
| | | [M + Na]+ | 898.2089 | 898.1991117 | $C_{36}H_{43}O_{25}Na$ |
| C1 | Luteolin 7-(6"-malonyl)glucoside | [M + H]+ | 535.1046 | 535.1087803 | $C_{24}H_{23}O_{14}$ |
| | | [M + Na]+ | 557.1089 | 557.0907253 | $C_{24}H_{22}O_{14}Na$ |
| C2 | Tricetin 7-(6"-malonyl)glucoside | [M + H]+ | 551.1034 | 551.1036949 | $C_{24}H_{23}O_{15}$ |
| | | [M + Na]+ | 573.0919 | 573.0856399 | $C_{24}H_{22}O_{15}Na$ | length than other anthocyanins under acidic conditions, under weakly acidic conditions the $\lambda_{vismax}$ shifted significantly toward the long wavelength end and violet color was exhibited. Since the $\lambda_{vismax}$ values for all of the petals were in a longer wavelength range than the $\lambda_{vismax}$ values for each of the major anthocyanins, it was conjectured that copigment substances contribute to a bathochromic shift and hyperchromic effect for flower color development in chrysanthemum, and especially the blue coloration.

Example 4: Search for Copigment Substances Exhibiting Blue Color by Coexistence with Delphinidin Glycosides Having Glucosyl Groups Bonded to 3'- and 5'-Hydroxyl Groups of B-Ring Using the cross-TLC method (NPL 8), a search was performed for copigment substances that interact with the major anthocyanins of transformants of "Taihei" chrysanthemum with blue petals. Approximately 200 mg of blue flower petals of gene recombinant chrysanthemum was crushed while frozen, and 500 µl of a 10% aqueous acetic acid solution was added to extract the components in the petals. A cellulose TLC glass plate (100×100 mm, Merck, Ltd.) was used for slanting cross loading and spreading of the extract, as previously reported (NPL 8). The spread TLC plate was developed at room temperature using a developing solvent BAW (n-butyl alcohol:acetic acid:water=4:1:2 (v/v/v)). The developed plate was air-dried and observed under a fluorescent lamp (LIGHTBOX NEW5000 inverter, Fujicolor) and under UV light (254/360 nm, CSN-15AC, Cosmo Bio Co., Ltd.), while being photographed with a digital camera. The Rf values of the anthocyanins were ternatin C5 (A8): 0.15; preternatin C5 (A7): 0.11; and Cy3MG3'G (A3): 0.30.

Figure 2:
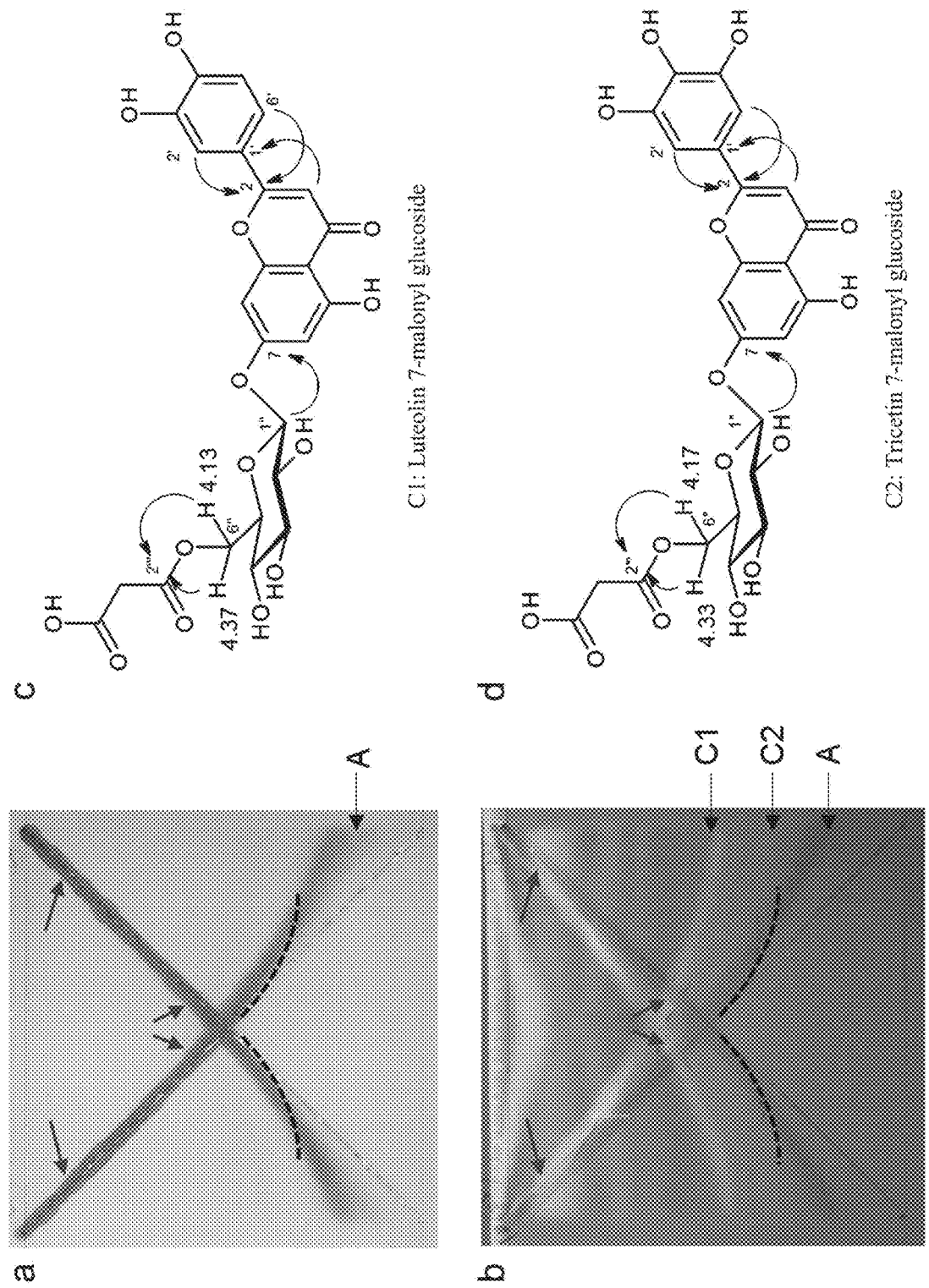

The development lines for anthocyanins had portions exhibiting red color, thought to be separated from the copigment, and portions exhibiting purple and blue color, thought to be coexisting with the copigment (FIG. 2a). With observation under UV light, bands exhibiting yellow fluorescence in the blue portions and dark bands in the purple portions were crossing (FIG. 2b). Presumably, coexistence of the copigments C1 and C2 in the respective bands with anthocyanins contributed to development of bluish color. As a result of extracting C1 and C2 from the TLC plate and analyzing them by UPLC-MS/MS, [M+H]$^+$=535 and [M+H]$^+$=551 were obtained, respectively.

Peaks for C1 and C2 having molecular weights of 535 and 551 were purified from blue chrysanthemum petal extract. Anthocyanins A7, A8 and A3 were also purified and isolated.

Example 5: Purification and Structural Identification of Copigments and Anthocyanin Glycosides Having Sugars Bonded to 3'- or 3'- and 5'-Hydroxyl Groups of B-Ring Blue chrysanthemum ray floret petals were collected and stored at −80° C. Approximately 2.5 kg of the frozen petals were crushed in liquid nitrogen, and soaked in approximately 5.9 L of a 10% formic acid aqueous solution for extraction of the components. The extracted petals were again subjected to extraction using 6 L of a 10% formic acid aqueous solution. The extract was filtered using a mesh filter (100 mesh), and then centrifuged for 10 minutes at 3,000 rpm to obtain a supernatant. The supernatant was injected into a column packed with 3 L of Diaion HP-20 resin (Mitsubishi Chemical Corp.). After rinsing the column with 9 L of a 0.1% formic acid aqueous solution, 0.1% formic acid-containing methanol was used for re-elution of the copigment and anthocyanins that had been adsorbed onto the resin. After concentrating the eluate, 14.2 g of the residue obtained by freeze-drying was dissolved in a 0.1% formic acid-containing 20% acetonitrile aqueous solution. The dissolved specimen was further detected at 360 nm and fractionated in a YMC-Pack ODS A (S-15 µm, 50 mm i.d.×250 mm) column at a flow rate of 30 ml/min, using a 0.1% formic acid-containing 20% acetonitrile aqueous solution as the solvent. Fraction 1 containing anthocyanins A7 (preternatin C5), A8 (ternatin C5) and A3 (Cy3MG3'G), fraction 2 containing copigment 2 (C2; Tr7MG) and fraction 3 containing copigment 1 (C1; Lt7MG) were each concentrated and freeze-dried and then re-dissolved in a 0.1% formic acid-containing 10% acetonitrile aqueous solution. Fraction 1 was further fractionated into fractions containing A3, A7 and A8 by preparative HPLC using 0.1% formic acid-containing 35% methanol as the solvent (flow rate: 30 ml/min, detection wavelength: 530 nm). A3, A7 and A8 were further fractionated and isolated by preparative HPLC using 0.5% formic acid-containing 20% methanol as the solvent (flow rate: 28 ml/min, detection wavelength: 530 nm).

C1 and C2 were further fractionated and isolated by preparative HPLC using 0.1% formic acid-containing 35% methanol as the solvent (flow rate: 30 ml/min, detection wavelength: 280 nm). The isolated copigments and anthocyanins were concentrated and freeze-dried, to obtain yellow powder (C1, Lt7MG: 201.5 mg; C2, Tr7MG: 52 mg) and dark red powder (A8, ternatin C5: 52 mg; A7, preternatin C5: 7 mg; A3, Cy3MG3'G: 9.8 mg).

The copigments C1 and C2 were dissolved in DMSO-d6. Anthocyanins A8 and A3 were respectively dissolved in a 10% (v/v) trifluoroacetic acid (TFA)-tetradeuteromethanol liquid mixture and a TFA-dimethyl sulfoxide-d6 (DMSO-d6) liquid mixture. The $^1$H-NMR, $^{13}$C-NMR, HMBC, HMQC and COSY spectra of the copigments, and the $^1$H-NMR and NOESY spectra of the anthocyanins were measured using a JNM-ECZ600R/S1 nuclear magnetic resonance apparatus (JEOL Ltd., Japan). The $^1$H and $^{13}$C resonance frequencies were 600.17 MHz and 150.91 MHz, respectively.

High-resolution mass spectrometry (HR-MS) of the purified copigments and anthocyanins was performed by linking an ESI-TOF-MS (JMS-T100LP, Jeol) with Agilent 1200 LC. The sample was dissolved in methanol to a concentration of 0.01 mg/ml, and 10-20 µl was injected. The analysis conditions were as follows: solvent: methanol; needle voltage: 2.2 kV; orifice 1 voltage: 85 V; orifice 2 voltage: 10 V; ring lens voltage: 25 V; peak tube voltage: 2 kV; dry gas flow rate: 1 L/min, nebulizer gas flow rate: 0.5 L/min; desolvation temperature: 250° C.; orifice 1 temperature, 80° C.

In the high-resolution mass spectrum of copigment 1 (C1), m/z values of 535.10457 (M+H)$^+$ and 557.10887 (M+Na)$^+$ were detected, which matched the masses calculated from the molecular formulas of $C_{24}H_{23}O_{14}$ (535.10878) and $C_{24}H_{22}O_{14}Na$ (557.09725) for Lt7MG. In the high-resolution mass spectrum of copigment 2 (C2), m/z values of 551.10341 (M+H)$^+$ and 573.09189 (M+Na)$^+$ were detected, which matched the masses calculated from the molecular formulas ($C_{24}H_{23}O_{15}$ (551.10369) and $C_{24}H_{22}O_{15}Na$ (573.08564)) for Tr7MG.

Based on analysis of the HR-MS spectra, $^1$H-NMR and $^{13}$C-NMR one-dimensional NMR spectra and HMBC, HMQC two-dimensional NMR spectra, the structure of C1 was determined to be luteolin 7-(6''-malonyl)glucoside (Lt7MG), and the structure of C2 was determined to be tricetin 7-(6''-malonyl)glucoside (Tr7MG) (FIGS. 2c and d, Tables 2 and 3).

TABLE 3

$^1$H (600 MHz) and $^{13}$C (150 MHz) NMR spectral data for flavone glucosides

| Position | C1 δH | C1 J(Hz) | C1 δC | C2 δH | C2 J(Hz) | C2 δC |
|---|---|---|---|---|---|---|
| Aglycone | | | | | | |
| 2 | — | | 164.8 | — | | 165.0 |
| 3 | 6.71 s | | 103.4 | 6.59 s | | 103.5 |
| 4 | — | | 182.2 | — | | 182.1 |
| 5 | — | | 161.4 | — | | 161.5 |
| 6 | 6.43 d | 1.4 | 99.8 | 6.44 d | 2.1 | 99.8 |
| 7 | — | | 162.9 | — | | 162.9 |
| 8 | 6.75 d | 1.4 | 94.9 | 6.70 d | 2.1 | 95.0 |
| 9 | — | | 157.2 | — | | 157.2 |
| 10 | — | | 105.7 | — | | 105.7 |
| 1' | — | | 121.7 | — | | 120.6 |
| 2' | 7.43 s | | 113.8 | 6.98 s | | 106.2 |
| 3' | — | | 146.1 | — | | 146.6 |
| 4' | — | | 150.2 | — | | 138.3 |
| 5' | 6.89 d | 8.4 | 116.2 | — | | 146.6 |
| 6' | 7.43 d | 8.4 | 119.3 | 6.98 s | | 106.2 |
| 5-OH | — | | — | — | | — |
| 4'-OH | — | | — | 9.15 br s | | — |
| 3'-OH | 9.94 br s | | — | 9.37 br s | | — |
| 5'-OH | — | | — | 9.37 br s | | — |
| Glucosyl | | | | | | |
| 1'' | 5.10 d | 7.6 | 99.9 | 5.10 d | 7.6 | 99.7 |
| 2'' | 3.28 m | | 73.3 | 3.28 t | 8.1 | 73.3 |
| 3'' | 3.31 m | | 76.4 | 3.33 t | 8.7 | 76.4 |
| 4'' | 3.19 t | 9.3 | 69.8 | 3.20 t | 9.0 | 69.8 |
| 5'' | 3.74 t | 7.8 | 74.1 | 3.74 dit. t | 9.3 | 74.0 |
| 6''-a | 4.37 d | 11.0 | 64.3 | 4.33 dd | 10.3 | 64.3 |
| 6''-b | 4.13 dd | 11.7, 6.9 | | 4.17 d | 12.1, 6.5 | |
| Malonyl | | | | | | |
| 1''' | — | | 167.1 | — | | 167.1 |
| 2'''-a | 3.32 d | 15.6 | 41.7 | 3.34 d | 15.6 | 41.6 |
| 2'''-b | 3.38 d | 15.6 | | 3.39 d | 15.6 | |
| 3''' | — | | 168.0 | — | | 168.1 |

Copigments (C1 and C2) in DMSO-d6.

Example 6: Reconstruction of Absorption Spectra for Blue Flower Petals by In Vitro Mixing of Delphinidin Glycosides Having Glucosyl Groups Bonded to 3'- and 5'-Hydroxyl Groups of B-Ring, and Copigments First, the anthocyanins and flavones in the blue chrysanthemum petals were analyzed and quantified by HPLC. Based on the values of the HPLC peak areas in the chromatograms obtained at a detection wavelength of 530 nm for the anthocyanins and a detection wavelength of 360 nm for the flavones, calibration curves for delphinidin 3-glucoside (anthocyanin) and luteolin (flavone) were used to calculate the amounts of compounds per petal (nmol/mg). As a result, the molar ratios of anthocyanins A7 to A9 having both the 3'- and 5'-positions glycosylated with respect to copigments C1 (Lt7MG) and C2 (Tr7MG) were an average of 1.0:1.7: 0.4 for the blue flower petals. The molar ratio of the total anthocyanin and total flavone amounts was an average of 1:5. Based on this ratio, mixtures were prepared with flavone-to-anthocyanin ratios of 1:1 to 1:10.

Next, approximately 5 g of ray floret petals was crushed in liquid nitrogen and then extracted with 15 ml of distilled water to obtain a juice solution. The juice solution was placed in a 15 ml tube and centrifuged at 8,000 rpm, 10° C. for 10 minutes, and the pH of the supernatant was measured with a D-71 pH meter (Horiba, Ltd.) equipped with a 9611-10D pH electrode. The flower color reconstruction experiment was carried out using acetate buffer at pH 5.6, which is the average pH of petal juice of "Taihei" transformants. The Lt7MG and Tr7MG purified copigments (flavones) were dissolved in dimethylsulfoxide (DMSO). The anthocyanins ternatin C5 (A8), Cy3MG3'G (A3), delphinidin 3-(6''-malonyl) glucoside (Dp3MG) (A5) and Cy3MG (A1) were dissolved in distilled water. Dp3MG was purified from mauve colored Clitoria petals. Cy3MG was synthesized and purified from reaction product of cyanidin 3-glucoside (Funakoshi Corp.) and malonyl-CoA (Sigma-Aldrich Corp.) by using a crude enzyme obtained from Clitoria petals.

Figure 3:
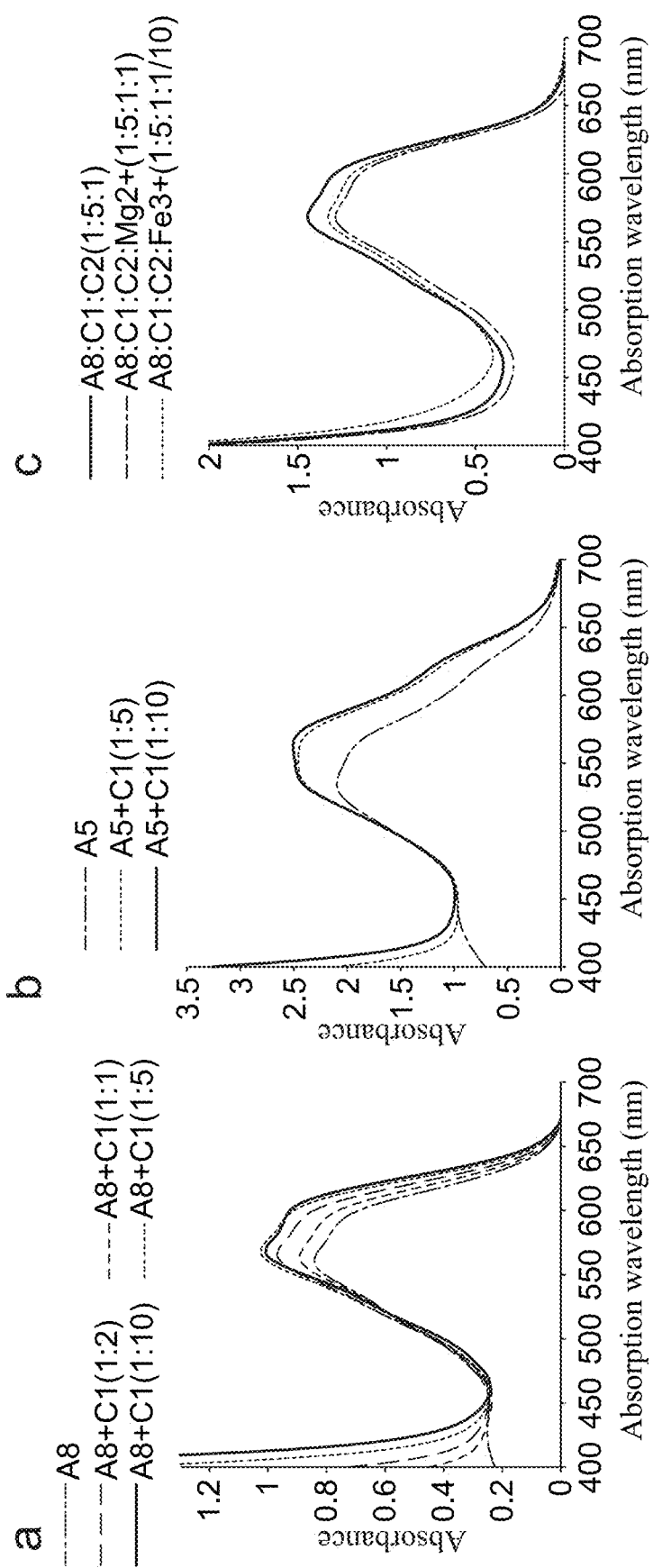
FIG. 3a shows the absorption spectrum in the visible light region of mixture solution containing a copigment and a major anthocyanin in blue chrysanthemum. As a result of mixing Lt7MG (C1) with ternatin C5 (TC5: A8), the absorbance at 600 to 620 nm characteristic of blue flower petals increased as the quantity ratio of TC5 increased from 1:1 to 1:5 or 1:10, while the absorption maximum wavelength also shifted to the long wavelength end, changing to an absorption spectrum similar to blue flower petals.
FIG. 3b shows the absorption spectrum in the visible light region of mixture solution containing a copigment and a major anthocyanin in purple/violet chrysanthemum. Addition of C1 to A5 increased the absorbance near 570 nm, exhibiting a spectral pattern similar to the absorption spectrum of purple petals.
FIG. 3c shows the absorption spectrum in the visible light region when C1 and C2 were added, with $Mg^{2+}$ ion added at an equivalent amount to A8 and $Fe^{3+}$ ion added at a 1/10 equivalent amount to A8.

After placing 100 mM acetate buffer (pH 5.6) (96-78 μl) in a 1.5 ml microtube, a 10 mM flavone DMSO solution (2-20 μl) was added and the components were uniformly dissolved. Next, a 10 mM anthocyanin aqueous solution (2 μl) was added and uniformly dissolved, and 100 μl of the reaction mixture was injected into a Super Micro Black Cell (optical path length: 10 mm, Shimadzu Corp.), and the absorption spectrum was measured using a UV-2450 spectrophotometer (Shimadzu Corp.). When addition was to a C1:A8 ratio of 1:1 to 1:10, increasing C1 proportion resulted in a shift of the absorption maximum wavelength and shoulder to the long wavelength end, and an increase in the absorbance at the absorption maximum wavelength (FIG. 3a). When C1 was added at 5 or more equivalents with respect to A8, a spectrum similar to blue flower petals was exhibited, with an absorption maximum wavelength at near 570 nm and a shoulder region at 600 to 620 nm, and the blue color hue was stronger (FIG. 3a). The same effect for blue color development was found with C2 as with C1. This demonstrated that the blue color development of chrysanthemum petals is achieved if C1 or C2 is present at 5 equivalents with respect to A8. Furthermore, addition of C1 to A5 increased the absorbance near 570 nm, exhibiting a spectral pattern similar to the absorption spectrum of purple petals (FIG. 3b). These results indicated that the same copigments are involved for development of purple/violet color as well.

An experiment with addition of magnesium ion and iron ion was carried out to examine the effects of metal ions on blue color development. The divalent magnesium salt magnesium acetate ($Mg(OAc)_2$) was dissolved in distilled water to a 10 mM concentration. The trivalent iron salt ammonium iron (III) sulfate ($FeNH_4 (SO_4)_2$) was dissolved in distilled water to a 1 mM concentration. A 2 µl portion of each aqueous metal ion solution was added to flavone-containing acetate buffer, after which the anthocyanin was added, and the absorption spectrum was measured for a final amount of 100 µl of the reaction mixture. No change was seen in the absorption spectrum pattern as a result of adding an equivalent of $Mg^{2+}$ ion to A8 or 1/10 equivalent of $Fe^{3+}$ ion to A8, in addition to C1 and C2 (FIG. 3c). It was thus demonstrated that metal ions do not participate, and that copigmentation with B-ring glycosylated anthocyanins and flavone glycosides is the major factor for blue color development in chrysanthemum.

Figure 4:
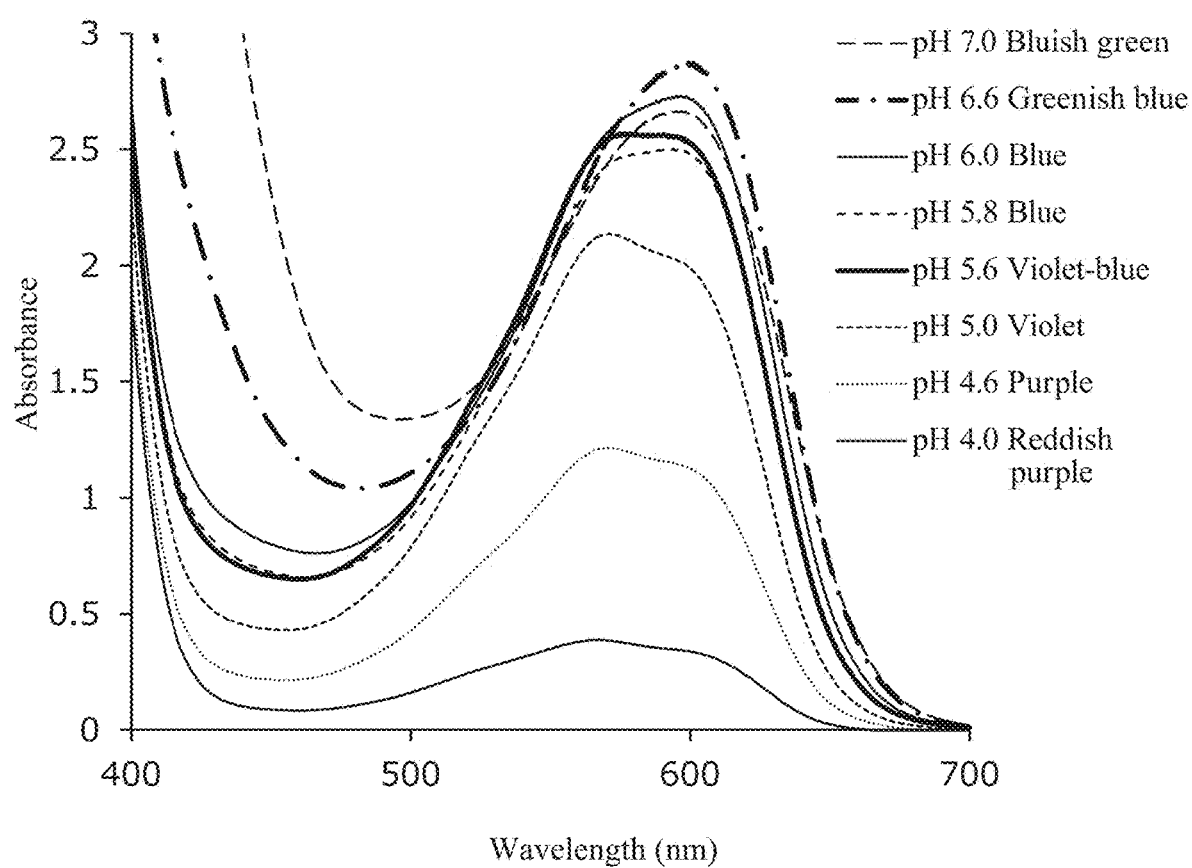
FIG. 4 shows the colors and absorption spectra for a mixture of a B-ring glycosylated anthocyanin (TC5) and flavone glycoside (Lt7MG) under different pH conditions (pH 4.0, 4.6, 5.0, 5.6, 5.8, 6.0, 6.6, 7.0).

Example 7: Effects of Different pH Conditions on Color Development in Copigmentation with Delphinidin Glycoside Having Glucosyl Groups Bonded to 3'- and 5'-Hydroxyl Groups of B-Ring, and Flavone Glycosides As a result of measuring the pH of flower petal juice of different chrysanthemum breeding lines and cultivars, and transformants, the values were found to be in the range of about 5.6 to 6.1. First, McIlvaine buffers mixed with a 0.2 M aqueous disodium hydrogenphosphate solution and a 0.1 M aqueous citric acid solution mixed to pH 5.6, 5.8 and 6.0 were used to examine the effect of pH on blue color development by copigmentation reaction with a B-ring glycosylated anthocyanin and a flavone glycoside. A8 (ternatin C5) was used as the B-ring glycosylated anthocyanin, and C1 (Lt7MG) was used as the flavone glycoside. McIlvaine buffer (88 µl) adjusted to each pH was placed in a 1.5 ml microtube, a 10 mM C1 DMSO solution (10 µl) was added and the mixture was uniformly dissolved. Next, a 10 mM A8 aqueous solution (2 µl) was added and uniformly dissolved, and 100 µl of the reaction mixture was injected into a Super Micro Black Cell (optical path length: 10 mm, Shimadzu Corp.), and the absorption spectrum was measured using a UV-2450 spectrophotometer (Shimadzu Corp.). As a result, the absorption maximum wavelength shifted more toward the long wavelength end (approximately 600 nm) at pH 5.8 than at pH 5.6, and the absorbance at near 600 nm increased at pH 6.0 (FIG. 4). This indicates that for cultivars, breeding lines and plant species in which the intravacuolar pH of the petals is 5.6, or even higher at 5.8 or 6.0, or under cultivation, storage and transport conditions where the intravacuolar pH is 5.8 or 6.0, coexistence of B-ring glycosylated anthocyanins and flavone glycosides allow more distinct blue color development.

The intravacuolar pH of anthocyanin accumulating flowers varies, being about 4 for hydrangea and about 7 for morning glory. Therefore, the effects of different pH conditions on color development by copigmentation were examined next. Using ternatin C5 as the 3',5'-glycosylated anthocyanin and C1 (Lt7MG) as the flavone glycoside copigment, they were mixed in a quantity ratio of 1:5. The buffer used was McIlvaine buffer (phosphate/citrate buffer) at pH 4.0, pH 4.6, pH 5.0, pH 5.6, pH 5.8, pH 6.0, pH 6.6 or pH 7.0. After adding 10 µL of a 10 mM flavone DMSO solution to 88 µL of buffer and mixing, 2 µL of a 10 mM aqueous anthocyanin solution was added and mixed. The reaction mixture was placed in a Super Micro Black Cell (Shimadzu Corp.), and the absorption spectrum at 400 to 700 nm was measured with a UV2450 (Shimadzu Corp.). As a result, at pH 5.6, an absorption spectrum pattern similar to blue chrysanthemum petals was exhibited, with an absorption maximum wavelength of near 577 nm with a shoulder at 590 to 596 nm, and absorption was also observed in a shoulder region of 600 to 620 nm, resulting in a slightly purplish blue color. At pH 5.8 to 6.0, the absorption maximum wavelength was 593 nm to 596 nm, resulting in a blue color. At pH 6.6 to 7.0, the absorption maximum wavelength was further shifted to the long wavelength end (597 to 598 nm), but the absorbance at 400 to 500 nm was high, resulting in a greenish blue to bluish green (turquoise) color. As the acidity increased from pH 5.6 to pH 4.0, the absorption maximum wavelength shifted toward the short wavelength end from 577 nm to 568 nm, while the absorbance was markedly reduced. The reaction mixture color also changed from blue to reddish purple. Based on these results, it was shown that the pH conditions suitable for development of blue color by copigmentation with B-ring glycosylated delphinidin-based anthocyanins and flavone glycosides are about 5.6 to 6.0, which are about the same as the pH range measured for blue chrysanthemum flower petal juice.

Figure 5:
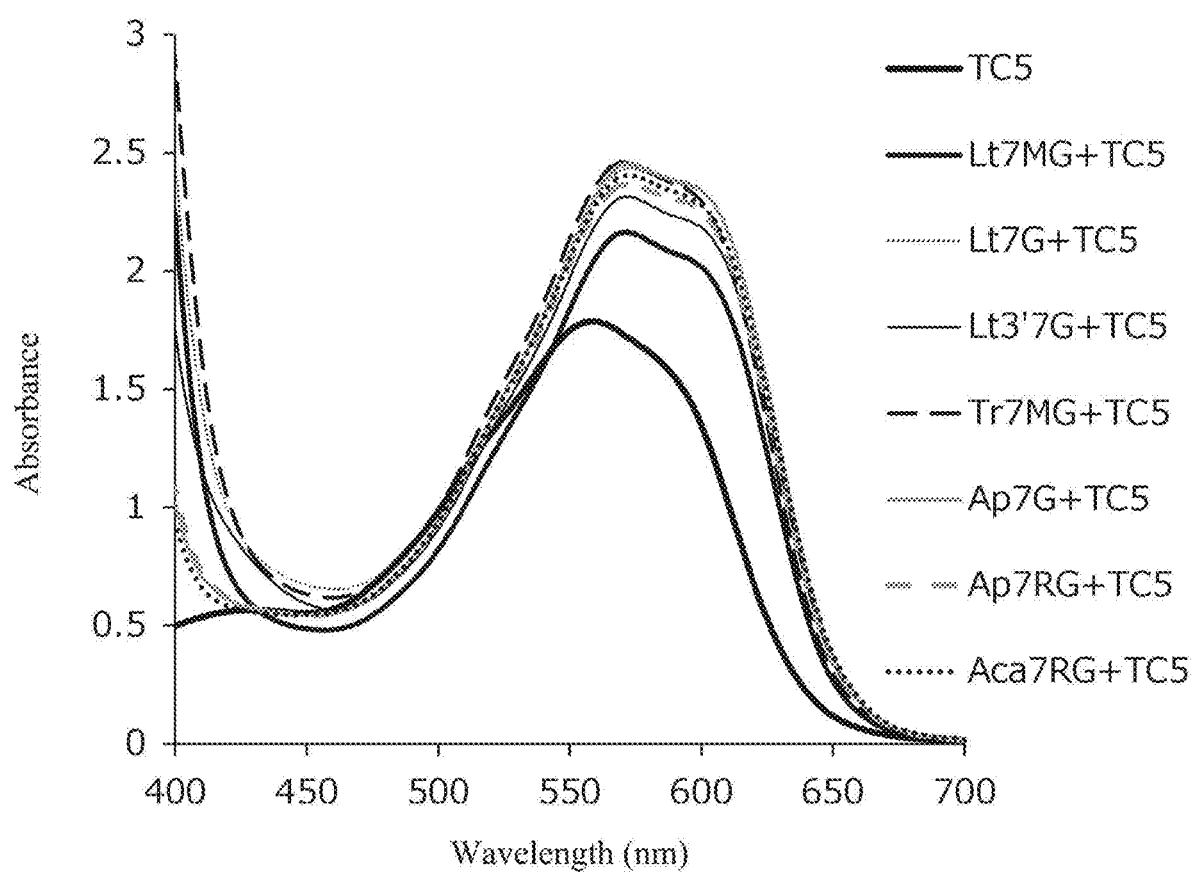
FIG. 5 shows the colors and absorption spectra for mixtures of a B-ring glycosylated anthocyanin (TC5) and different flavone glycosides (Lt7MG, Lt7G, Lt3'7G, Tr7MG, Ap7G, Ap7RG, Aca7RG).

Example 8: Effects on Color Development by Differences in Structures of Flavone Glycosides that Cause Copigmentation with B-Ring-Glycosylated Delphinidin-Based Anthocyanins In a cross-TLC method, flavone glycosides were used that had different structures from Lt7MG and Tr7MG, which had been demonstrated to be copigments that develop blue color by coexistence with 3',5'-glycosylated delphinidin-based anthocyanins in blue chrysanthemum petals, and their effects on B-ring-glycosylated delphinidin-based anthocyanin color development were examined. Ternatin C5 dissolved in distilled water was used as the anthocyanin. As flavone glycosides, apigenin 7-glucoside and 7-rutinoside that are hydroxylated only at the 4'-position of the B-ring, acacetin 7-rutinoside that is hydroxylated at the 4'-position of the B-ring and methoxylated at the 3'-position, luteolin 7-glucoside, 7-(6"-malonyl)glucoside (Lt7MG) and 3',7-diglucoside that are hydroxylated at the 3'-position and 4'-position of the B-ring, and Tr7MG that is hydroxylated at the 3'-position, 4'-position and 5'-position of the B-ring, were dissolved in DMSO. After adding 10 µL of a 10 mM flavone DMSO solution to 88 µL of acetate buffer at pH 5.6 and mixing, 2 µL of a 10 mM aqueous anthocyanin solution was added, and the anthocyanin and flavone were mixed in a quantity ratio of 1:5. The reaction mixture was placed in a Super Micro Black Cell (Shimadzu Corp.), and the absorption spectrum at 400 to 700 nm was measured with a UV2450 (Shimadzu Corp.). As a result, the absorption maximum wavelength with dissolution of ternatin C5 alone was 559 nm, but with tested all of the flavone glycosides for copigmentation with ternatin C5, a spectral pattern with an absorption maximum wavelength of 572 to 574 nm and a shoulder at 595 to 597 nm was exhibited, and blue color was developed (FIG. 5). These results showed that differences in the modification pattern by hydroxyl groups and methoxyl groups at the 3'-position and 5'-position of the flavone B-ring, differences in the glycosyl residues at the 7-hydroxyl group, or the presence or absence of a malonyl group at the 7-glucosyl group, do not produce any significant change in blue color development by copigmentation. This suggests that all of the 3',5'-glycosylated delphinidin-based anthocyanins and all of the flavone glycosides in blue chrysanthemum petals participate in copigmentation to develop blue color. Moreover, it indicates that blue color can be developed by accumulation of 3',5'-glycosylated delphinidin-based anthocyanins even in other plant species that synthesize flavone glycosides with different structures than chrysanthemum flavone glycosides in their flowers.

Figure 6:
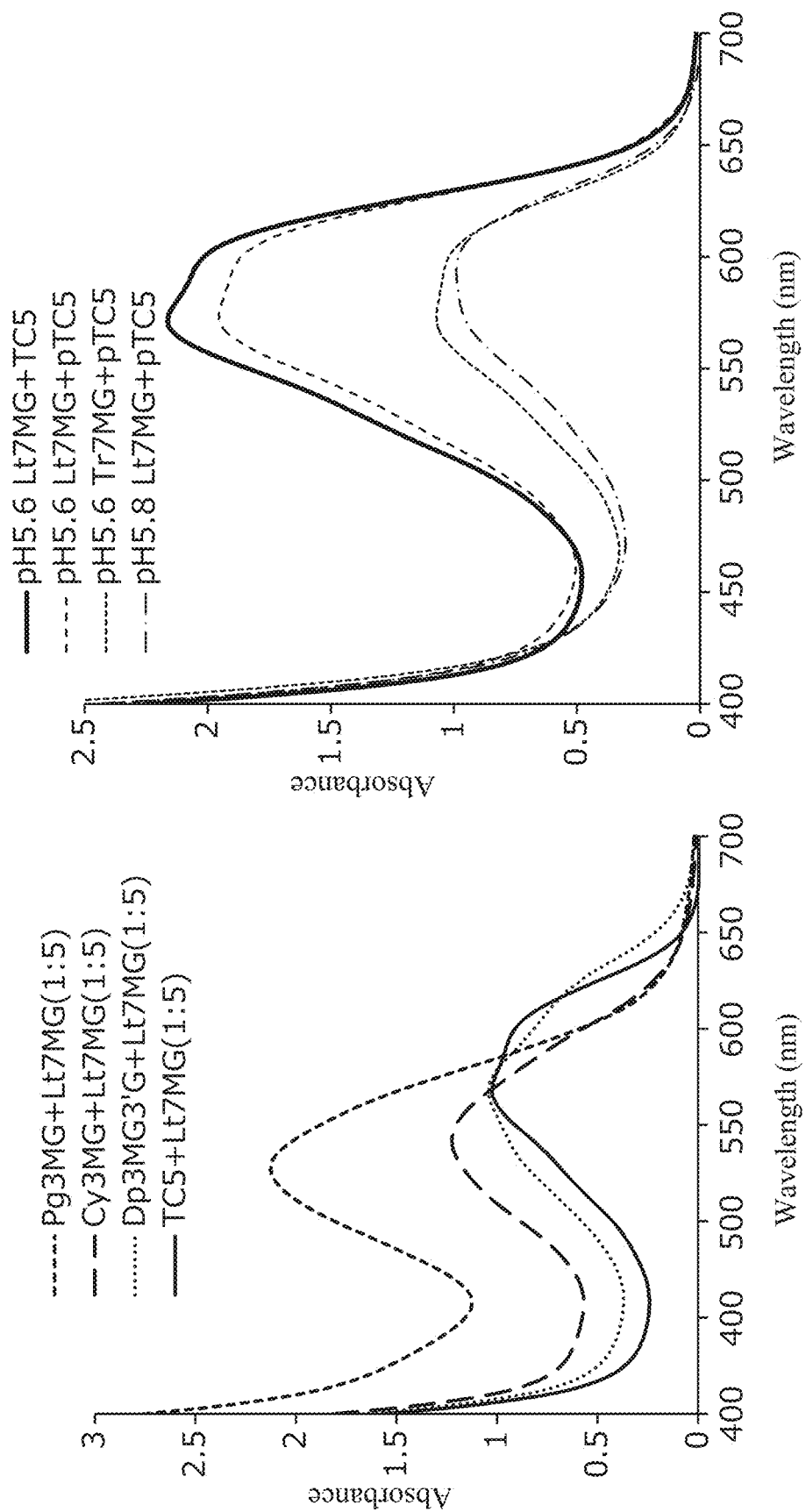
FIG. 6 shows the absorption spectra for mixtures of anthocyanins with different B-ring modification patterns (Pg3MG, Cy3MG, Dp3MG3'G, TC5) and a flavone glycoside (Lt7MG) (left). Also shown are the absorption spectra for anthocyanin and flavone glycoside mixtures under different conditions (Lt7MG+TC5 (pH 5.6), Lt7MG+pTC5 (pH 5.6), Tr7MG+pTC5 (pH 5.6), Lt7MG+pTC5 (pH 5.8)) (right).

Example 9: Effects on Copigmentation-Dependent Color Development by Differences in Modification Pattern of Anthocyanin B-Ring The structural features of anthocyanins that develop blue color by copigmentation in coexistence with Lt7MG were examined. Pelargonidin 3-(6''-malonyl) glucoside (Pg3MG), Cy3MG, delphinidin 3-(6''-malonyl) glucoside-3'-glucoside (Dp3MG3'G) and ternatin C5 (TC5) were used as anthocyanins. As shown at left in FIG. 6, a blue color-developing spectrum was not obtained with Pg3MG in which the 3'-position and 5'-position of the anthocyanin B-ring are not modified, and Cy3MG in which the 3'-position is hydroxylated. Although the absorption maximum value was approximately the same with Dp3MG3'G lacking the 5'-glucosyl group of TC5 that exhibits blue color, the spectrum exhibited had low absorbance from the shoulder at 600 nm up to about 620 nm, while instead, a shoulder region was observed at the short wavelength end near 530 nm. This indicated that glycosylations of both of the hydroxyl groups at the 3'- and 5'-positions of anthocyanins are important for blue color development by copigmentation with flavone glycosides.

Example 10: Effect on Copigmentation-Dependent Color Development by Presence or Absence of Malonyl Group of 3-Glucose of 3',5'-Diglycosylated Delphinidin-Based Anthocyanins The effect of the presence or absence of a malonyl group at the 3-glucose of 3',5'-glycosylated delphinidin-based anthocyanins, during copigmentation with flavone glycosides, on blue color development was examined. Ternatin C5 (TC5) and preternatin C5 (pTC5) were used as anthocyanins, and Lt7MG and Tr7MG were used as flavone glycoside copigments. Preternatin C5 purified from chrysanthemum blue flower petals was used after confirming the structure by LC-MS/MS. The anthocyanin and flavone were mixed in a quantity ratio of 1:5. After adding 10 µL of a 10 mM flavone DMSO solution to 88 µL of acetate buffer at pH 5.6 and mixing, 2 µL of a 10 mM aqueous anthocyanin solution was added and mixed. The reaction mixture was placed in a Super Micro Black Cell (Shimadzu Corp.), and the absorption spectrum at 400 to 700 nm was measured with a UV2450 (Shimadzu Corp.). As a result, as shown at right in FIG. 6, even when a malonyl group was not present at the 3-glucose of the anthocyanin (Lt7MG+pTC5), a spectral pattern with an absorption maximum wavelength of 572 nm and a shoulder near 595 nm was exhibited, similar to when it was present (Lt7MG+TC5), and blue color was developed. Also, when the pH was changed from 5.6 to 5.8, the absorption maximum wavelength shifted from 572 nm to 594 nm, and blue color was exhibited. On the other hand, discoloration in the pTC5 mixed solution was markedly more rapid compared to TC5 which has a malonyl group, suggesting that modification by a malonyl group at the 3-glucose of the anthocyanin is necessary for more stable development of blue color.

Figure 7:
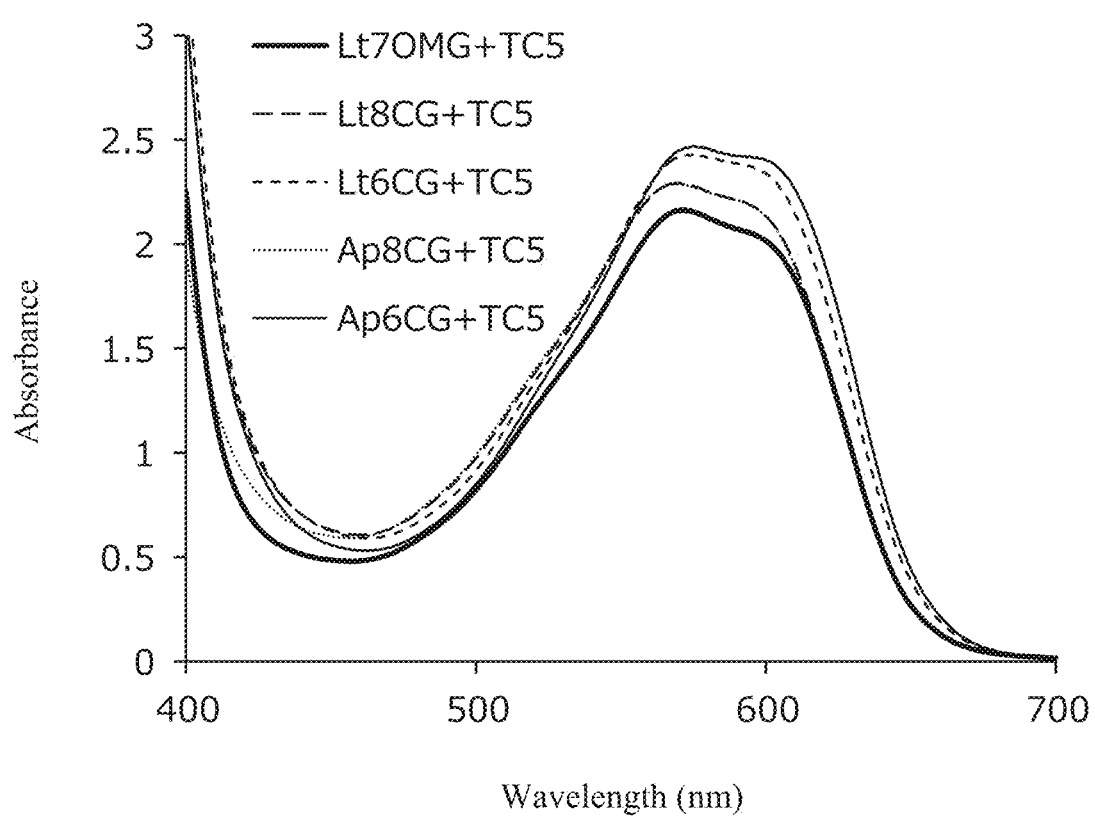
FIG. 7 shows the absorption spectra for mixtures of a B-ring glycosylated anthocyanin (TC5) and different flavone glycosides (Lt7OMG=Lt7MG (C1), Lt8CG, Lt6CG, Ap8CG, Ap6CG).

Example 11: Copigmentation-Dependent Color Development with 3',5'-Diglycosylated Delphinidin-Based Anthocyanin and C-Glucosylated Flavones The effects of the bonding form of glycosyl groups in flavone glycoside copigments on blue color development was examined using C-glycosylated flavones (Funakoshi Corp.). Ternatin C5 was used as a 3',5'-diglycosylated anthocyanin, and 5 different copigments were used: Lt7MG (Lt7OMG) having an O-bonding glucosyl group bonded at the 7-position of flavone aglycone, and luteolin 8-C-glucoside (orientin, Lt8CG), luteolin 6-C-glucoside (homoorientin, isoorientin, Lt6CG), apigenin 8-C-glucoside (vitexin, Ap8CG), apigenin 6-C-glucoside (isovitexin and Ap6CG), having C-bonding glucosyl groups at the 6- or 8-position of flavone aglycone. The anthocyanin and flavone were mixed in a quantity ratio of 1:5. After adding 10 µL of a 10 mM flavone DMSO solution to 88 µL of acetate buffer at pH 5.6 and mixing, 2 µL of a 10 mM aqueous anthocyanin solution was added and mixed. The reaction mixture was placed in a Super Micro Black Cell (Shimadzu Corp.), and the absorption spectrum at 400 to 700 nm was measured with a UV2450 (Shimadzu Corp.). As a result, as shown in FIG. 7, with Lt8CG and Ap8CG having glucosyl group C-bonding at the 8-position, the absorption maximum and shoulder were both shifted several nm to the short wavelength end compared to Lt7OMG, and violet-blue color resulted. On the other hand, with Lt6CG and Ap6CG having glucosyl group C-bonding at the 6-position, the absorption maximum was shifted about 3 nm to the long wavelength end compared to Lt7OMG, and absorbance at the shoulder near 595 nm was also increased. Particularly with Ap6CG (isovitexin), a peak appeared at 595 nm, and a more stable and distinct blue color was developed than in Lt7OMG or the other C-glycosyl flavones. This result indicates that coexistence of a flavone glycoside having glucose C-bonded at the 6-position is effective for development of the blue color of 3',5'-diglycosylated delphinidin-based anthocyanins.

Figure 8:
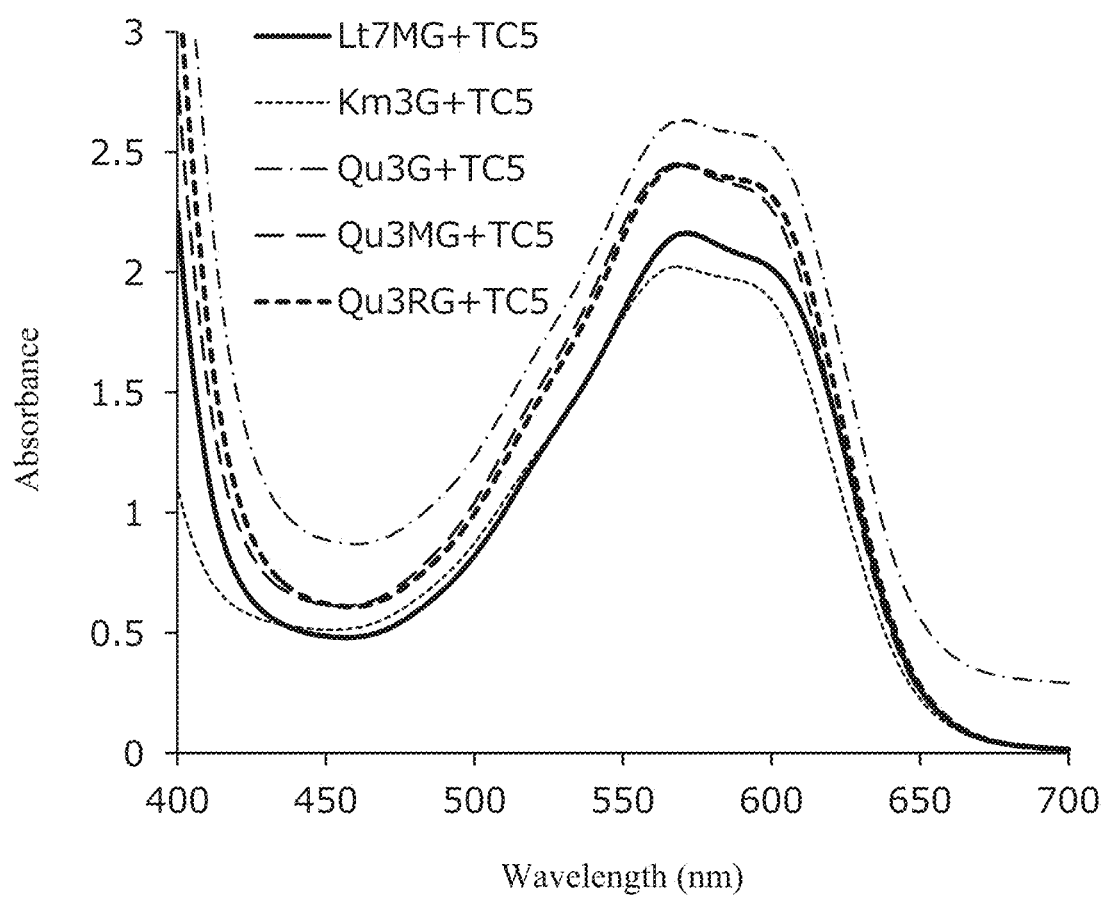
FIG. 8 shows the absorption spectra for mixtures of a B-ring glycosylated anthocyanin (TC5) and a flavone glycoside (Lt7MG) or different flavonol glycosides (Km3G, Qu3G, Qu3MG, Qu3RG).

Example 12: Copigmentation-Dependent Color Development with 3',5'-Diglycosylated Delphinidin-Based Anthocyanin and Flavonol Glycosides Using many flavonol glycosides reported to accumulate with anthocyanins in the flower petals, similar to flavone glycosides, as copigments, their effects on copigmentation-dependent blue color development were examined. Ternatin C5 was used as the 3',5'-diglycosylated anthocyanin, and the copigments used were the flavonol glycosides: kaempferol 3-glucoside (Km3G), quercetin 3-glucoside (Qu3G), quercetin 3-malonyl glucoside (Qu3MG) and quercetin 3-rutinoside (rutin, Qu3RG), and the flavone Lt7MG. The anthocyanin and flavonol or flavone were mixed in a quantity ratio of 1:5. After adding 104 of a 10 mM flavonol DMSO solution or flavone DMSO solution to 88 µL of acetate buffer at pH 5.6 and mixing, 2 µL of a 10 mM aqueous anthocyanin solution was added and mixed. The reaction mixture was placed in a Super Micro Black Cell (Shimadzu Corp.), and the absorption spectrum at 400 to 700 nm was measured with a UV2450 (Shimadzu Corp.). As a result, as shown in FIG. 8, with the flavone Lt7MG, an absorption spectral pattern was exhibited having an absorption maximum wavelength of 572 nm and a shoulder near −595 nm, and blue color was exhibited. On the other hand, with the flavonols Km3G, Qu3MG and Qu3RG, the absorption maximum shifted to the short wavelength end of 568 to 569 nm with the shoulder also near 592 mm, and the color was a more purplish blue than with Lt7MG. Among the 4 flavonols examined, Qu3G had an absorption spectrum closest to that obtained with flavone Lt7MG as the copigment, and its absorption maximum wavelength and shoulder positions were approximately the same. These results suggested that not only flavones but also flavonols can develop blue color or violet-blue color by copigmentation with 3',5'-diglycosylated delphinidin-based anthocyanins.

The invention claimed is:
1. A method of creating a plant with a blue flower color, the method comprising the step of transforming the cells of the plant to express a *Campanula*-derived flavonoid 3',5'-hydroxylase transgene (CamF3'5'H) and a *Clitoria*-derived anthocyanin 3',5'-O-glucosyltransferase transgene (CtA3'5'GT) so that delphinidin-based anthocyanins having glycosyl-residues at both the 3'- and 5'-positions of the anthocyanin B-ring coexist with a flavone glycoside or flavonol glycoside in the cells of the plant,
wherein the transformation is carried out by:
introducing the *Clitoria*-derived anthocyanin 3',5'-O-glucosyltransferase transgene into the cells of the plant;
further introducing the *Campanula*-derived flavonoid 3',5'-hydroxylase transgene into the cells of the plant when the cells of the plant do not accumulate any delphinidin-based anthocyanins; and
further optionally introducing a flavone synthase transgene or a flavonol synthase transgene into the cells of the plant when the cells of the plant do not accumulate any flavone glycosides or flavonol glycosides,
wherein the plant is rose, lily, carnation, dahlia, *Phalaenopsis aphrodite*, or chrysanthemum,
wherein the delphinidin-based anthocyanins having glycosyl groups at both the 3'- and 5'-positions of the anthocyanin B-ring and the flavone glycoside or the flavonol glycoside coexist in a quantity ratio of 1:5 to 1:10, and wherein the intravacuolar pH in the cells of the plant is 5.2 to 6.4.
2. The method according to claim 1, wherein the flavone glycoside is selected from the group consisting of luteolin glycoside, tricetin glycoside, apigenin glycoside, acacetin glycoside, and their combinations.
3. The method according to claim 2, wherein the luteolin glycoside is luteolin 7-malonyl glucoside, luteolin 7-glucoside, luteolin 7,3'-diglucoside, luteolin 8-C-glucoside, luteolin 6-C-glucoside, or a derivative thereof.
4. The method according to claim 2, wherein the tricetin glycoside is tricetin 7-malonyl glucoside or a derivative thereof.
5. The method according to claim 2, wherein the apigenin glycoside is apigenin 7-glucoside, apigenin 7-rutinoside, apigenin 8-C-glucoside, apigenin 6-C-glucoside, or a derivative thereof.
6. The method according to claim 2, wherein the acacetin glycoside is acacetin 7-rutinoside or a derivative thereof.
7. The method according to claim 1, wherein the flavonol glycoside is selected from the group consisting of kaempferol glycoside, quercetin glycoside, and their combinations.
8. The method according to claim 7, wherein the kaempferol glycoside is kaempferol 3-glucoside or a derivative thereof.
9. The method according to claim 7, wherein the quercetin glycoside is quercetin 3-glucoside, quercetin 3-(6"-malonyl) glucoside, quercetin 3-rutinoside, or a derivative thereof.
10. The method according to claim 1, wherein the delphinidin-based anthocyanins having glycosyl groups at both the 3'- and 5'-positions of the anthocyanin B-ring are selected from the group consisting of delphinidin 3-(6"-malonyl)glucoside-3',5'-diglucoside (ternatin C5), delphinidin 3,3',5'-triglucoside (preternatin C5), and their combinations.
11. The method according to claim 1, wherein the plant is rose.
12. A transformed plant with a blue flower color, its inbred progeny, or its outbred progeny, wherein the plant is rose, lily, carnation, dahlia, *Phalaenopsis aphrodite*, or chrysanthemum,
wherein the cells of the transform plant, the inbred progeny, or the outbred progeny express a *Campanula*-derived flavonoid 3',5'-hydroxylase transgene (CamF3'5'H) and a *Clitoria*-derived anthocyanin 3',5'-O-glucosyltransferase transgene (CtA3'5'GT),
wherein delphinidin-based anthocyanins having glycosyl groups at both the 3'- and 5'-positions of the anthocyanin B-ring coexist with a copigment, in a quantity ratio of 1:5 to 1:10, in the cells of the transformed plant, the inbred progeny, or the outbred progeny,
wherein the copigment is a flavone glycoside or a flavonol glycoside, and
wherein the intravacuolar pH of the cells of the transformed plant is 5.2 to 6.4.
13. The transformed plant, its inbred progeny, or its outbred progeny according to claim 12, wherein the flavone glycoside is selected from the group consisting of luteolin glycoside, tricetin glycoside, apigenin glycoside, acacetin glycoside, and their combinations.
14. The transformed plant, its inbred progeny, or its outbred progeny according to claim 13, wherein the luteolin glycoside is luteolin 7-malonyl glucoside, luteolin 7-glucoside, luteolin 7,3'-diglucoside, luteolin 8-C-glucoside, luteolin 6-C-glucoside, or a derivative thereof.
15. The transformed plant, its inbred progeny, or its outbred progeny according to claim 13, wherein the tricetin glycoside is tricetin 7-malonyl glucoside or a derivative thereof.
16. The transformed plant, its inbred progeny, or its outbred progeny according to claim 13, wherein the apigenin glycoside is apigenin 7-glucoside, apigenin 7-rutinoside, apigenin 8-C-glucoside, apigenin 6-C-glucoside, or a derivative thereof.
17. The transformed plant, its inbred progeny, or its outbred progeny according to claim 13, wherein the acacetin glycoside is acacetin 7-rutinoside or a derivative thereof.
18. The transformed plant, its inbred progeny, or its outbred progeny according to claim 12, wherein the flavonol glycoside is selected from the group consisting of kaempferol glycoside, quercetin glycoside, and their combinations.

19. The transformed plant, its inbred progeny, or its outbred progeny according to claim 18, wherein the kaempferol glycoside is kaempferol 3-glucoside or a derivative thereof.

20. The transformed plant, its inbred progeny, or its outbred progeny according to claim 18, wherein the quercetin glycoside is quercetin 3-glucoside, quercetin 3-(6"-malonyl) glucoside, quercetin 3-rutinoside, or a derivative thereof.

21. The transformed plant, its inbred progeny, or its outbred progeny according to claim 12, wherein the delphinidin-based anthocyanins having glycosyl groups at both the 3'- and 5'-positions of the anthocyanin B-ring are selected from the group consisting of delphinidin 3-(6"-malonyl)glucoside-3',5'-diglucoside (ternatin C5), delphinidin 3,3',5'-triglucoside (preternatin C5), and their combinations.

22. The transformed plant, its inbred progeny, or its outbred progeny according to claim 12, wherein the plant is rose.

23. Propagules, partial plant bodies, tissue or cells of the transformed plant, its inbred progeny, or its outbred progeny according to claim 12.

24. Cut flowers of the transformed plant, its inbred progeny, or its outbred progeny of claim 12, or a processed form created from the cut flowers.

* * * * *